US011424006B2

(12) United States Patent
Apte et al.

(10) Patent No.: US 11,424,006 B2
(45) Date of Patent: Aug. 23, 2022

(54) TARGETED DRUGS ASSOCIATED WITH TRIMETHYLAMINE AND/OR TRIMEIHYLAMINE-N-OXIDE

(71) Applicant: Psomagen, Inc., Rockville, MD (US)

(72) Inventors: Zachary Apte, San Francisco, CA (US); Jessica Richman, San Francisco, CA (US); Daniel Almonacid, San Francisco, CA (US); Valeria Marquez, San Francisco, CA (US); Ingrid Araya, San Francisco, CA (US); Melissa Alegria, San Francisco, CA (US); Mario Saavedra, San Francisco, CA (US); Luis Gomez, San Francisco, CA (US); Janyra Espinoza, San Francisco, CA (US); Javier Gimpel, San Franscisco, CA (US); Eduardo Morales, San Francisco, CA (US); Rodrigo Ortiz, San Francisco, CA (US)

(73) Assignee: Psomagen, Inc., Rockville, MD (US)

(*) Notice: Subject to any disclaimer, the term of this patent is extended or adjusted under 35 U.S.C. 154(b) by 0 days.

(21) Appl. No.: 16/638,779

(22) PCT Filed: Aug. 14, 2018

(86) PCT No.: PCT/US2018/046764
§ 371 (c)(1),
(2) Date: Feb. 13, 2020

(87) PCT Pub. No.: WO2019/036507
PCT Pub. Date: Feb. 21, 2019

(65) Prior Publication Data

US 2021/0128498 A1 May 6, 2021

Related U.S. Application Data

(60) Provisional application No. 62/545,065, filed on Aug. 14, 2017, provisional application No. 62/545,056, filed on Aug. 14, 2017.

(51) Int. Cl.
*G16B 15/00* (2019.01)
*G16B 5/00* (2019.01)
(Continued)

(52) U.S. Cl.
CPC ............ *G16B 15/00* (2019.02); *A61K 31/015* (2013.01); *A61K 31/045* (2013.01); *A61K 31/047* (2013.01); *A61K 31/05* (2013.01); *A61K 31/075* (2013.01); *A61K 31/085* (2013.01); *A61K 31/11* (2013.01); *A61K 31/12* (2013.01); *A61K 31/121* (2013.01); *A61K 31/122* (2013.01); *A61K 31/133* (2013.01); *A61K 31/136* (2013.01); *A61K 31/14* (2013.01); *A61K 31/15* (2013.01); *A61K 31/16* (2013.01); *A61K 31/164* (2013.01); *A61K 31/165* (2013.01); *A61K 31/166* (2013.01); *A61K 31/167* (2013.01); *A61K 31/185* (2013.01); *A61K 31/192* (2013.01); *A61K 31/198* (2013.01); *A61K 31/216* (2013.01); *A61K 31/22* (2013.01); *A61K 31/222* (2013.01); *A61K 31/235* (2013.01); *A61K 31/26* (2013.01); *A61K 31/277* (2013.01); *A61K 31/336* (2013.01); *A61K 31/341* (2013.01); *A61K 31/343* (2013.01); *A61K 31/357* (2013.01); *A61K 31/36* (2013.01); *A61K 31/365* (2013.01); *A61K 31/37* (2013.01); *A61K 31/381* (2013.01); *A61K 31/40* (2013.01); *A61K 31/404* (2013.01); *A61K 31/4015* (2013.01); *A61K 31/4035* (2013.01); *A61K 31/41* (2013.01); *A61K 31/415* (2013.01); *A61K 31/4192* (2013.01); *A61K 31/4196* (2013.01); *A61K 31/42* (2013.01); *A61K 31/428* (2013.01); *A61K 31/4245* (2013.01); *A61K 31/437* (2013.01); *A61K 31/439* (2013.01); *A61K 31/4355* (2013.01); *A61K 31/44* (2013.01);
(Continued)

(58) Field of Classification Search
None
See application file for complete search history.

(56) References Cited

U.S. PATENT DOCUMENTS

| | | | | |
|---|---|---|---|---|
| 8,005,620 B2 * | 8/2011 | Gustafsson | G16B 20/00 703/2 |
| 8,635,029 B2 * | 1/2014 | Gustafsson | G16B 20/20 707/700 |

(Continued)

FOREIGN PATENT DOCUMENTS

| | | |
|---|---|---|
| WO | 2013/188417 A2 | 12/2013 |
| WO | 2016/049537 A1 | 3/2016 |

OTHER PUBLICATIONS

Henrich et al., "On the use of PIPSA to Guide Target-Selective Drug Design", 2008, ChemMedChem, 3(3), pp. 413-417. (DOI: 10.1002/cmdc.200700154) (Year: 2008).*

(Continued)

*Primary Examiner* — My-Chau T. Tran
(74) *Attorney, Agent, or Firm* — Morgan, Lewis & Bockius LLP

(57) ABSTRACT

Embodiments of a method and/or system can include administering, to a patient with one or more conditions associated with at least one of TMA, TMAO, and/or derivatives thereof, a therapeutically effective amount of a compound for affecting inhibiting one or more CutC enzymes and/or CntA enzymes associated with microorganisms from at least one taxon from a set of microorganism taxa.

11 Claims, 3 Drawing Sheets

(51) Int. Cl.

| | |
|---|---|
| *A61K 31/047* | (2006.01) |
| *A61P 9/10* | (2006.01) |
| *A61K 31/40* | (2006.01) |
| *A61K 31/045* | (2006.01) |
| *A61K 31/4409* | (2006.01) |
| *A61K 31/166* | (2006.01) |
| *A61K 31/05* | (2006.01) |
| *A61K 31/4196* | (2006.01) |
| *A61K 31/12* | (2006.01) |
| *A61K 31/14* | (2006.01) |
| *A61K 31/415* | (2006.01) |
| *A61K 31/192* | (2006.01) |
| *A61K 31/4406* | (2006.01) |
| *A61K 31/216* | (2006.01) |
| *G16B 15/30* | (2019.01) |
| *A61K 31/015* | (2006.01) |
| *A61P 31/04* | (2006.01) |
| *A61P 13/12* | (2006.01) |
| *A61K 31/075* | (2006.01) |
| *A61K 31/085* | (2006.01) |
| *A61K 31/11* | (2006.01) |
| *A61K 31/121* | (2006.01) |
| *A61K 31/122* | (2006.01) |
| *A61K 31/133* | (2006.01) |
| *A61K 31/136* | (2006.01) |
| *A61K 31/15* | (2006.01) |
| *A61K 31/16* | (2006.01) |
| *A61K 31/164* | (2006.01) |
| *A61K 31/165* | (2006.01) |
| *A61K 31/167* | (2006.01) |
| *A61K 31/185* | (2006.01) |
| *A61K 31/198* | (2006.01) |
| *A61K 31/22* | (2006.01) |
| *A61K 31/222* | (2006.01) |
| *A61K 31/235* | (2006.01) |
| *A61K 31/26* | (2006.01) |
| *A61K 31/277* | (2006.01) |
| *A61K 31/336* | (2006.01) |
| *A61K 31/341* | (2006.01) |
| *A61K 31/343* | (2006.01) |
| *A61K 31/357* | (2006.01) |
| *A61K 31/36* | (2006.01) |
| *A61K 31/365* | (2006.01) |
| *A61K 31/37* | (2006.01) |
| *A61K 31/381* | (2006.01) |
| *A61K 31/4015* | (2006.01) |
| *A61K 31/4035* | (2006.01) |
| *A61K 31/404* | (2006.01) |
| *A61K 31/41* | (2006.01) |
| *A61K 31/4192* | (2006.01) |
| *A61K 31/42* | (2006.01) |
| *A61K 31/4245* | (2006.01) |
| *A61K 31/428* | (2006.01) |
| *A61K 31/4355* | (2006.01) |
| *A61K 31/437* | (2006.01) |
| *A61K 31/439* | (2006.01) |
| *A61K 31/44* | (2006.01) |
| *A61K 31/4402* | (2006.01) |
| *A61K 31/4418* | (2006.01) |
| *A61K 31/4425* | (2006.01) |
| *A61K 31/4465* | (2006.01) |
| *A61K 31/50* | (2006.01) |
| *A61K 31/502* | (2006.01) |
| *A61K 31/517* | (2006.01) |
| A61P 1/12 | (2006.01) |

(52) U.S. Cl.

CPC ...... *A61K 31/4402* (2013.01); *A61K 31/4406* (2013.01); *A61K 31/4409* (2013.01); *A61K 31/4418* (2013.01); *A61K 31/4425* (2013.01); *A61K 31/4465* (2013.01); *A61K 31/50* (2013.01); *A61K 31/502* (2013.01); *A61K 31/517* (2013.01); *A61P 9/10* (2018.01); *A61P 13/12* (2018.01); *A61P 31/04* (2018.01); *G16B 5/00* (2019.02); *G16B 15/30* (2019.02)

(56) References Cited

U.S. PATENT DOCUMENTS

| | | | | |
|---|---|---|---|---|
| 2015/0134315 | A1* | 5/2015 | Sarmiento .............. | G16C 10/00 703/11 |
| 2017/0152222 | A1 | 6/2017 | Garcia-Garcia | |
| 2019/0050525 | A1* | 2/2019 | Apte .................... | A61K 31/439 |

OTHER PUBLICATIONS

David Hecht, "Applications of Machine Learning and Computational Intelligence to Drug Discovery and Development", Feb. 2011, Drug Development Research, 72(1), pp. 53-65. (DOI: 10.1002/ddr.20402) (Year: 2011).*

Ning et al., "In Silico Structure-Activity-Relationship (SAR) Models From Machine Learning: A Review", Mar. 2011, Drug Development Research, 72(2), pp. 138-146 (DOI: 10.1002/ddr.20410) (Year: 2011).*

File History of related U.S. Appl. No. 16/103,830 retrieved Sep. 13, 2021.

Wang et al., "Non-lethal Inhibition of Gut Microbial Trimethylamine Production of for the Treatment of Atherosclerosis," Cell, Cell Press, vol. 163, No. 7, pp. 1588-1590, Dec. 17, 2015.

Zhu et al., "Gut Microbial Metabolite TMAO Enhances Platelet Hyperreactivity and Thrombosis Risk," Cell, Cell Press, vol. 165, No. 1, pp. 111-124, Mar. 10, 2016.

Rath et al., "Uncovering the trimethylamine-producing bacteria of the human gut microbiota," Microbiome, Biomed Central Ltd., vol. 5, No. 1, pp. 1-14, May 15, 2017.

International Search Report and Written Opinion issued in International Application No. PCT/US2018/046764, dated Dec. 21, 2018.

* cited by examiner

TARGETED DRUGS ASSOCIATED WITH TRIMETHYLAMINE AND/OR TRIMEIHYLAMINE-N-OXIDE

CROSS-REFERENCE TO RELATED APPLICATIONS

This application is the U.S. National Phase under 35 U.S.C. § 371 of International Application No. PCT/US2018/046764 filed on Aug. 14, 2018, which claims the benefit of U.S. Provisional Application No. 62/545,056 filed on Aug. 14, 2017 and U.S. Provisional Application No. 62/545,065 filed Aug. 14, 2017, which are each incorporated in their entirety herein by reference.

TECHNICAL FIELD

The disclosure generally relates to microbiology.

BACKGROUND

The concept of drugging microbial targets (e.g., drugging the microbiome, etc.) can include one or more therapeutic approaches avoiding targeting human cells directly, and/or avoiding side effects derived from gene therapy; and instead targeting receptors and enzymes belonging to microbiota. Such approaches can avoid knocking-down the action of human enzymes by gene therapy methods, where such enzymes are not only possibly involved in the production of undesirable metabolites, but can also exert beneficial effects on the organism.

Choline is a crucial nutrient for humans and other organisms, contributing to different roles in biological pathways as cell membrane function, methyl transfer events, and neurotransmission. In addition to choline, the trimethylamine (TMA) metabolite is an important source of nitrogen, and it is also a carbon source for bacteria that convert TMA in greenhouse gas methane in marine environments. These small molecules are connected through the choline trimethylamine-lyase (CutC) enzyme, which is a glycine radical enzyme that performs the cleavage of the C—N bond in choline to produce trimethylamine (TMA) and acetaldehyde as follows: Choline=trimethylamine+acetaldehyde.

Gut bacteria and/or other suitable microorganisms from any suitable body sites can play a critical role in triggering and progression of some diseases. Human gut microbiota has been described as producing TMA from choline; a process that is exclusively found in microbes. Choline degradation is the major source of TMA formation within the intestines. Specifically, gut bacteria diet can have an incidence on the production of TMA and its derivative product trimethylamine-N-oxide (TMAO). For example, TMA metabolite, which is often obtained from meat, egg (e.g., egg yolk, etc.), fat-rich food, and/or dairy products is absorbed and converted to TMAO in the liver by the action of the human. Flavin-containing monooxygenase 3 (FMO3) enzyme.

Patients having high TMA levels display higher probabilities of suffering a heart attack. These aspects have become particularly relevant when recent studies have discarded that saturated fats and cholesterol are correlated with an increased risk of heart diseases and atherosclerosis.

TMAO is a metabolite that has been associated with a high risk of cardiovascular and renal diseases, and additionally, high levels of TMAO produced from choline can trigger atherosclerosis in mice. Two main TMA synthesis pathways have been described in bacteria, one using choline as a substrate (CutC/CutD complex) and the other one using L-carnitine (the two-component Rieske-type oxygenase/reductase CntA/B). Genes encoding CntA/B have been described in several taxa belonging to Betaproteobacteria as well as from a few *Firmicutes.*

Regarding one of the main TMA synthesis pathways described, the pathway uses choline as a substrate (CutC/CutD complex). TMA is absorbed and is converted in the liver to TMAO by the action of the FMO3 enzyme. FMO3 participates in host-gut microbiota metabolic interactions. Some strategies have proposed to knock-down the expression of FMO3 enzymes using antisense oligonucleotides that inhibit transcription of its mRNA. While directly reducing choline or L-carnitine ingestion may produce undesired effects, since these molecules can be beneficial in lower quantities, inhibiting FMO3 enzyme to reduce TMAO levels can also undesirable, because accumulation of TMA produces (e.g., through suppression of FMO3 enzymes) conditions or side effects such as hepatic inflammation and/or trimethylaminuria (e.g., fish odor syndrome; fish malodor disorder; etc.).

DESCRIPTION OF THE EMBODIMENTS

The following description of the embodiments is not intended to limit the embodiments, but rather to enable any person skilled in the art to make and use.

1. Overview

Figure 1:
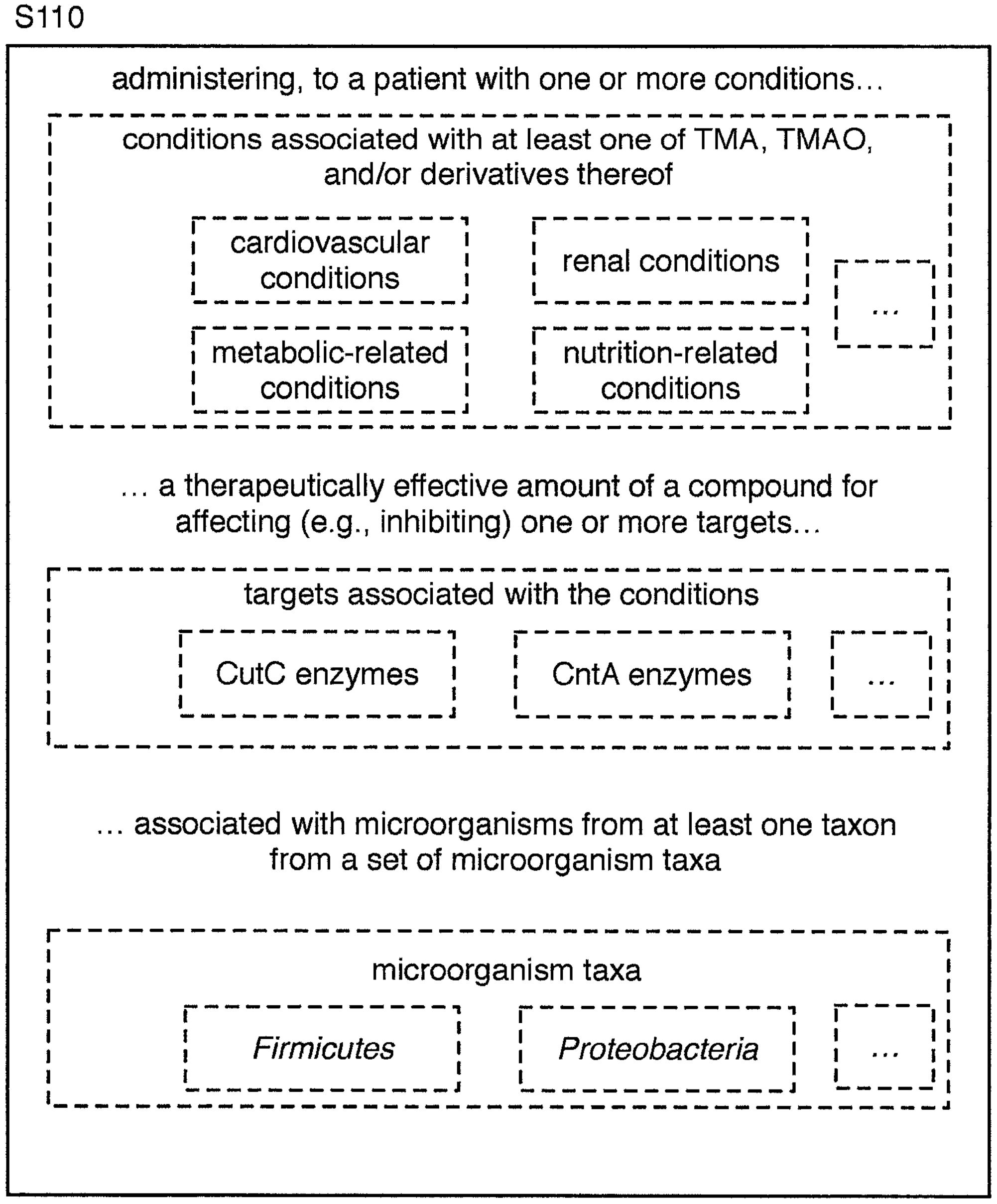
FIG. 1 includes a flowchart representation of variations of an embodiment of a method.
Figure 2:
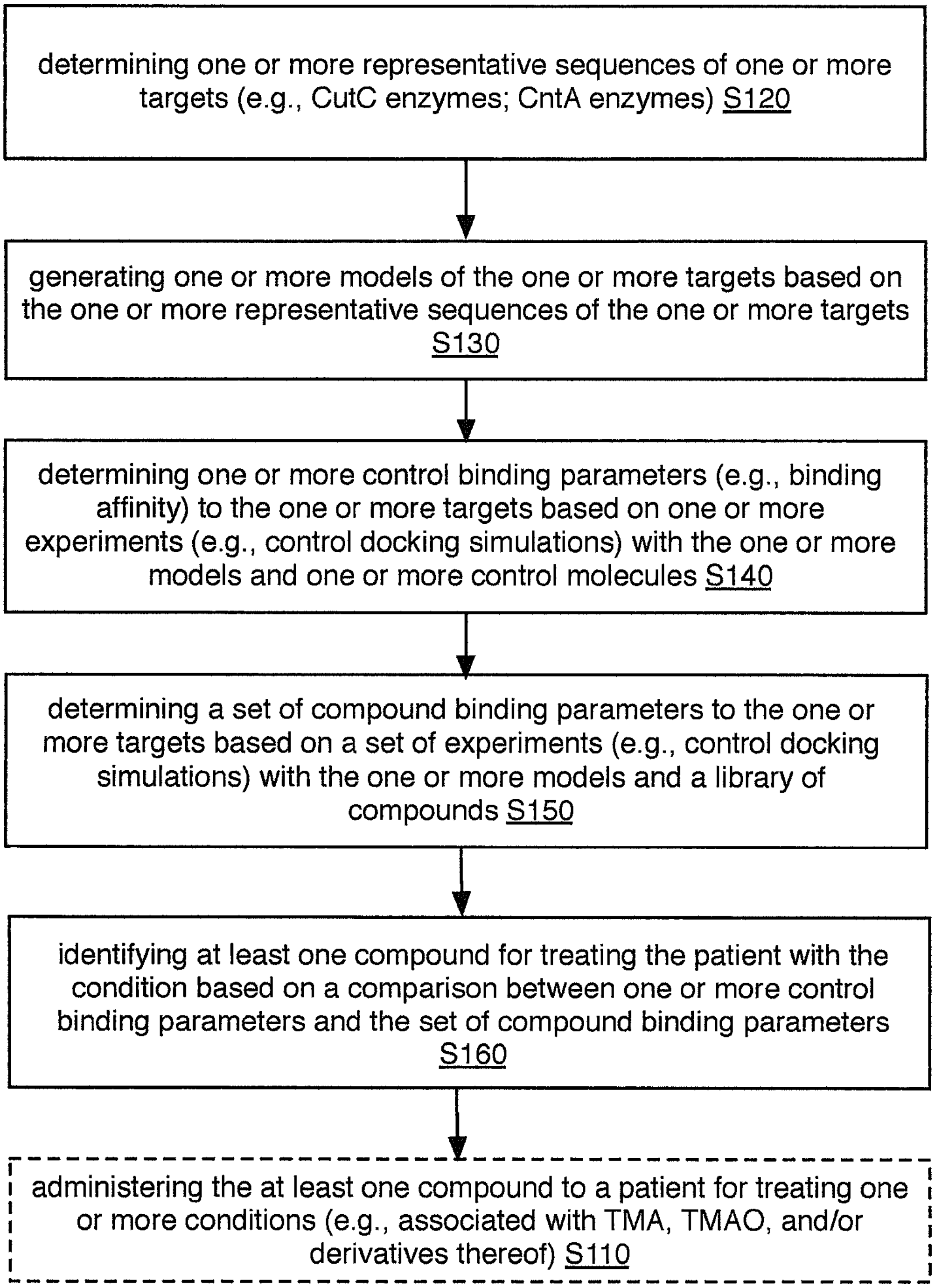
FIG. 2 includes a flowchart representation of variations of an embodiment of a method.
Figure 3:
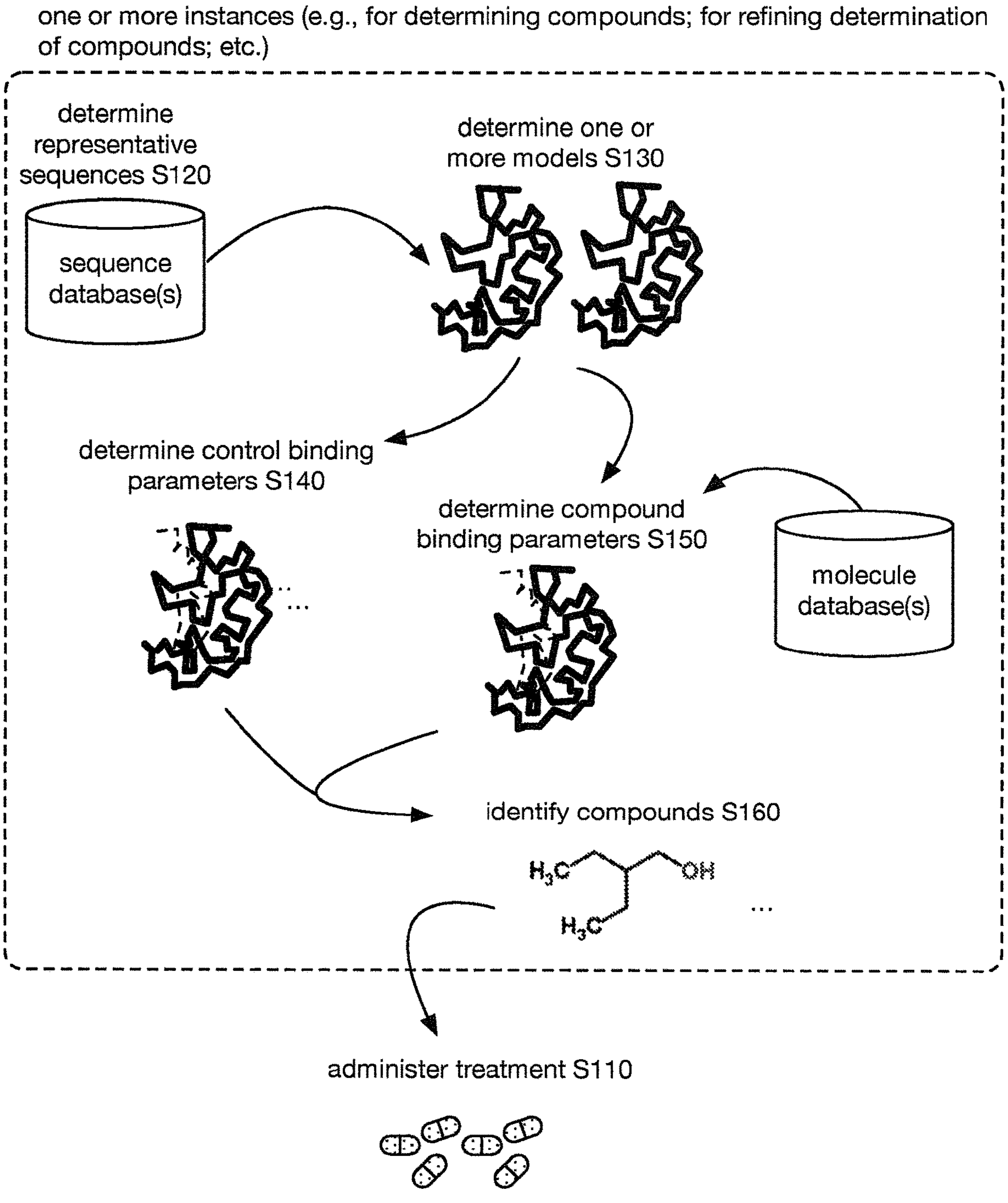
FIG. 3 includes a graphical representation of variations of an embodiment of a method.

As shown in FIGS. 1-3, embodiments of a method 100 (e.g., for treating a patient with a condition associated with at least one of TMA, TMAO, and/or derivatives thereof; etc.) can include administering, to a patient with one or more conditions (e.g., one or more conditions associated with the at least one of TMA, TMAO, and/or derivatives thereof; etc.), a therapeutically effective amount of a compound (e.g., drug; etc.) for affecting (e.g., inhibiting; etc.) one or more targets S110 (e.g., CutC enzymes; Rieske-type oxygenase (CntA) enzymes; other enzymes; proteins; other biological targets; non-biological targets; enzymes associated with at least one of TMA, TMAO, and/or derivatives thereof; etc.) associated with microorganisms from at least one taxon from a set of microorganism taxa (e.g., from at least one of *Firmicutes* (phylum) and *Proteobacteria* (phylum); etc.).

In an example, a method 100 (e.g., for treating a patient with one or more conditions associated with at least one of TMA, TMAO, and/or derivatives thereof; etc.) can include administering, to the patient with the one or more conditions, a therapeutically effective amount of a compound for inhibiting CutC enzymes of microorganisms from at least one of *Firmicutes* (phylum) and *Proteobacteria* (phylum), where the compound (e.g., including one or more constituents, such as any suitable combination of constituents; etc.) includes at least one of: 2-Ethyl-1-butanol; (2R)-3,3-Dimethyl-1,2-butanediol; (2S)-3,3-Dimethyl-1,2-butanediol; (2S)-4-Methyl-2-pentanol; (2S)-3-Methyl-2-butanol; (2R)-4-Methyl-2-pentanol; (2R)-3-Methyl-2-butanol; (2S)-2-Pentanol; (2S)-2-Methyl-1,4-butanediol; 2-Methyl-2,4-butanediol; Trimethylolpropane; 3-(4-Methoxyphenyl)

propanal; 1-(3-Pyridinyl)-2-propanamine; 2-[(2R)-2-Butanyl]phenol; 4-Propylbenzoic acid; (2S)-1-(Benzyloxy)-2-propanol; Methyl 3-(4-hydroxyphenyl)propanoate; α-Methylphenylalanine; 2,2-Dimethyl-1-phenyl-1-propanol; Methyl (2R)-hydroxy(phenyl)acetate; (2S)-2-Phenylpyrrolidinium; 4-Methyl-3-phenyl-1,2-oxazol-5-amine; 4,4'-Biphenyldiamine; 4'-Methyl-2-biphenylcarbonitrile; 4-Biphenylol; 2-[3-(4-Methylphenyl)-1,2-oxazol-5-yl]ethanol; 4-Biphenylcarboxamide; 4-Ethynylbiphenyl; 5-(4-Methylphenyl)-1H-1,2,4-triazol-3-amine; 5-(4-Methylphenyl)-1H-pyrazol-3-amine; 4-Hydroxycatechol; 3-Phenyl-1H-pyrazole-5-carbohydrazide; 4-Methyl-1,3-benzenediol; N-(2-Hydroxyethyl)-1,3-propanediaminium; 3-Methoxy-3-methylbutanol; 4-Pyridinylmethanaminium; N-Methyl-3-pyridinamine; 2-Methoxypyridine; 5-Methyl-3-pyridinamine; 1-(4-Methyl-3-pyridinyl)methanamine; Mesitylene; (E)-Benzaldoxime' (3R)-2,2,4-Trimethyl-1,3-pentanediol; (1R,4R)-2-Azabicyclo[2.2.1]hept-2-ylacetic acid; 3-ACETYLPHENOL; 3-Hydroxybenzoicacid; 1H-Indol-7-ylmethanol; 3-Vinylaniline; (3s,5s,7s)-1-Isocyanatoadamantane; (1R,2S,5R)-2-Hydroxy-2,6,6-trimethylbicyclo[3.1.1]heptan-3-one; (−)-β-Pinene; 2H-Isoindole-1,3-diamine; (3s,5s,7s)-1-Adamantanol; (3-Aminobicyclo[2.2.1]hept-2-yl)methanol; 3-(Hydrazinomethyl)phenol; (1S,2R)-2-Carbamoylcyclohexanaminium; (1S,4R)-1,3,3-Trimethylbicyclo[2.2.1]heptan-2-one; Trimethylbicyclo[2.2.1]heptan-2-one; Methyl 4-methyl-4-piperidinecarboxylate; Methyl heptanoate; 3-Methylpyridazine; 4,5-Dimethyl-1,2-oxazol-3-amine; 2-(2-Hydroxyethoxy)phenol; 2-Hydroxy-N-(3-pyridinylmethyl)ethanaminium; 3-Phenyl-1-propanol; (2R)-6-Methyl-2-heptanol; 2-Phenoxyacetohydrazide; N-Hydroxyoctanamid; Cyclobutanecarbohydrazide; Phenylhydrazine; (1S,4R)-2-Azabicyclo[2.2.1]hept-5-en-3-one; salicylamide; Adamantane; 3-Azabicyclo[3.3.1]nonane; N-Hydroxy-2-methylbenzenecarboximiamide; (−)-camphene; (1S,2S,4S)-Bicyclo[2.2.1]hept-5-en-2-ylmethanol; Dicyclopentadiene; (8-anti)-3-Azabicyclo[3.2.1]octan-8-ol; (1R,2S,6R,7S)-Tricyclo[5.2.1.02,6]deca-3,8-diene; any suitable compounds including any suitable combination of any suitable compounds and/or structures (e.g., of one or more structures; etc.) included in Tables 1-4; and/or any pharmaceutically acceptable forms thereof; and/or salts of thereof.

In an example, a method 100 (e.g., for treating a patient with one or more conditions associated with at least one of TMA, TMAO, and/or derivatives thereof; etc.) can include administering, to the patient with the one or more conditions, a therapeutically effective amount of a compound for inhibiting CntA enzymes of microorganisms from at least one of *Firmicutes* (phylum) and *Proteobacteria* (phylum), where the compound (e.g., including one or more constituents, such as any suitable combination of constituents; etc.) includes at least one of: N-Methylglutamic acid; 4-(1-Pyrrolidinyl)butanoic acid; 4-Methyl-4-piperidinecarboxylic acid; Isonipecotic acid; N-propylbenzene; N-Ethyl-2-pyridinamine; (4R)-4-Amino-1-propyl-2-pyrrolidinone; 2,5-Diaminotoluene; Ethyl phenyl ether; Phenylcyanate; 1-(2-Cyclopenten-1-yl)acetone; 2-Amino-3-methylpyridinium; E-pyridine-3-aldoxime; N-Cyclohexylformamide; 2-Methyl-2-hexenoic acid; 4-Heptanaminium; 3,4-Anhydro-3-carboxy-2-deoxy-L-threo-pentaric acid; 2,2'-[(2-Hydroxyethyl)imino]diacetic acid; 1H-Tetrazol-5-ylacetic acid; Diacetylacetone; (2S)-2-Acetoxypropanoic acid; 4,4'-Biphthalic anhydride; Bis(1H-benzotriazol-1-yl)methanone; 2-Anthraquinonesulfonic acid; 3-(1,3-Dioxo-1,3-dihydro-2H-isoindol-2-yl)benzonitrile; 2-phenylquinazolin-4-ol; 4-Amino-2-(1,3-benzothiazol-2-yl)phenol; 4-Phenyl-1(2H)-phthalazinone; 5-(1,3-Benzodioxol-5-yl)-2-methyl-3-furoic acid; (5R)-5(2-Naphthyl)dihydro-2(3H)-furanone; 3-[5-(3-Methylphenyl)-1,3,4-oxadiazol-2-yl]propanoic acid; 9-ETHYNYLPHENANTHRENE; PHA-767491; 3-Amino-2-methylphenol; 5-(4-Methylphenyl)-2-furoic acid; 8-Methyl-4H-thieno[3,2-c]chromene-2-carboxylic acid; resorcinol monobenzoate; 3-Methoxy-4-biphenylcarbaldehyde; (7-Amino-4-methyl-2-oxo-2H-chromen-3-yl)acetic acid; 2,3-Dihydro-1H-inden-5-yl(oxo)acetic acid; 3-(2-Pyridyl)aniline; 4-(3-Methyl-1H-1,2,4-triazol-5-yl)aniline; Benzidine; (DL)-3-O-Methyldopa; Methyl (2E)-3-(2-amino-5-methyl-3-pyridinyl)acrylate; (5-Methylfuro[2,3-b]pyridin-2-yl)methanol; (2R)-2,3-Dihydro-1,4-benzodioxin-2-ylmethanaminium; R-phenylethyl propionate; i-propyl benzoate; 4-Acetotoluide; (1S)-1-(2,5-Dimethylphenyl)ethanaminium; (1R)-2-Methyl-2,5-cyclohexadiene-1-carboxylic acid; (2,2-Dimethoxyethyl)benzene; any suitable compounds including any suitable combination of any suitable compounds and/or structures (e.g., of one or more structures; etc.) included in Tables 5-8; and pharmaceutically acceptable forms thereof; and/or salts of thereof.

Additionally or alternatively, as shown in FIGS. 2-3, embodiments of the method 100 (e.g., for identifying at least one compound for treating a patient with a condition associated with at least one of TMA, TMAO, and/or derivatives thereof; etc.) can include determining one or more representative sequences (e.g., nucleic acid sequence; amino acid sequence; etc.) of one or more targets (e.g., CutC enzymes; CntA enzymes; other enzymes; proteins; other biological targets; non-biological targets; enzymes associated with at least one of TMA, TMAO, and/or derivatives thereof; etc.) S120, such as where the one or more representative sequences are representative of one or more sets of sequences of the one or more targets for at least one taxon of a set of microorganism taxa (e.g., a representative sequence representative of a plurality of sequences of the target from a plurality of different taxa, such as from *Firmicutes* (phylum) and *Proteobacteria* (phylum); etc.); generating one or more models (e.g., protein structure models; etc.) of the one or more targets based on the one or more representative sequences of the one or more targets S130; determining one or more control binding parameters (and/or other suitable interaction parameters; etc.) to the one or more targets based on one or more experiments (e.g., control docking simulations; other computational simulations; other experiments; etc.) with the one or more models and one or more control molecules (e.g., 3,3-dimethyl-1-butanol; L-carnitine; etc.) S140; determining a set of compound binding parameters (and/or other suitable interaction parameters; etc.) to the one or more targets based on a set of experiments (e.g., control docking simulations; other computational simulations; other experiments; etc.) with the one or more models and a library of compounds (e.g., with the potential to affect the one or more targets, such as the potential to inhibit CutC enzymes and/or CntA enzymes; etc.) S150; identifying at least one compound (e.g., from the library of compounds; etc.) for treating the patient with the condition associated with the at least one of TMA, TMAO, and derivatives thereof, based on a comparison between one or more control binding parameters (and/or other suitable interaction parameters associated with the one or more control molecules; etc.) and the set of compound binding parameters (and/or other suitable interaction parameters associated with the compounds; etc.) S160; and/or validating one or more compounds S170.

Embodiments of the method 100 and/or system 200 can function to diagnose and/or treat one or more patients with one or more conditions associated with at least one of TMA, TMAO, and/or derivatives thereof, such as by using and/or administering (and/or other suitable provision and/or promotion) of one or more compounds affecting one or more targets (e.g., inhibiting CutC enzymes; inhibiting CntA enzymes; etc.) associated with the one or more conditions (e.g., correlated with, causative; etc.) and/or associated with microorganisms from at least one taxon from a set of taxa (e.g., from at least one of *Firmicutes* (phylum) and *Proteobacteria* (phylum); etc.). Additionally or alternatively, embodiments of the method 100 and/or system 200 can function to identify one or more compounds that can be administered for treating one or more patients with one or more conditions (e.g., associated with at least one of TMA, TMAO, and/or derivatives thereof; etc.).

In an example, the method 100 can screen libraries of compounds (e.g., including any suitable number of compounds; etc.), based on molecular docking simulations, for identifying compounds (e.g., drugs; etc.) that can bind the active site of one or more targets (e.g., CutC enzymes; CntA enzymes; etc.) from microorganisms (e.g., from *Firmicutes* (phylum) and/or *Proteobacteria* (phylum); etc.) and associated with TMA, TMAO, and/or derivatives thereof, such as for identifying compounds with therapeutic effects (e.g., by inhibiting production of TMA; TMAO; derivatives thereof; etc.) on conditions associated with TMA, TMAO, and/or derivatives thereof. In an example, the method 100 can overcome side effects and/or complications associated with inhibiting FMO3 enzyme, such as by selectively inhibiting pathways producing TMA, such as CutC/CutD and/or CntA/CntB.

Conditions (e.g., treatable by the one or more compounds; etc.) preferably include conditions associated with characterizations and/or therapies for one or more microorganism-related conditions associated with at least one of TMA, TMAO, and/or derivatives thereof (e.g., conditions triggerable, caused by, correlated with, and/or otherwise associated with one or more of TMA, TMAO, and/or derivatives thereof, such as a high amounts of TMA, TMAO, and/or derivatives thereof; etc.). Conditions associated with at least one of TMA, TMAO, and/or derivatives thereof can include any one or more of: cardiovascular conditions (e.g., atherosclerosis; severe heart failure; coronary heart disease; inflammatory heart disease; valvular heart disease; obesity; stroke; thrombosis, platelet responsiveness, etc.); renal conditions (e.g., renal failure; chronic kidney disease; polycystic kidney disease; glomerulonephritis; IgA nephropathy; nephritis; nephrotic syndrome; lupus; kidney cancer; rare kidney diseases; etc.); metabolic-related conditions (e.g., trimethylaminuria (TMAU); etc.); nutrition-related conditions (e.g., weight-related conditions such as weight-loss conditions; blood sugar-related conditions such as high blood sugar-related conditions; allergy-related conditions such as allergies and/or intolerance associated with wheat, gluten, dairy, soy, peanut, shellfish, tree nut, egg; etc.).

Additionally or alternatively, conditions can include any one or more of: gastrointestinal-related conditions (e.g., irritable bowel syndrome, inflammatory bowel disease, ulcerative colitis, celiac disease, Crohn's disease, bloating, hemorrhoidal disease, constipation, reflux, bloody stool, diarrhea, etc.); skin-related conditions (e.g., acne, dermatomyositis, eczema, rosacea, dry skin, psoriasis, dandruff, photosensitivity, rough skin, itching, flaking, scaling, peeling, fine lines or cracks, gray skin in individuals with dark skin, redness, deep cracks such as cracks that can bleed and lead to infections, itching and scaling of the skin in the scalp, oily skin such as irritated oily skin, skin sensitivity to products such as hair care products, imbalance in scalp microbiome, etc.); locomotor-related conditions (e.g., gout, rheumatoid arthritis, osteoarthritis, reactive arthritis, multiple sclerosis, Parkinson's disease, etc.); cancer-related conditions (e.g., lymphoma; leukemia; blastoma; germ cell tumor; carcinoma; sarcoma; breast cancer; prostate cancer; basal cell cancer; skin cancer; colon cancer; lung cancer; cancer conditions associated with any suitable physiological region; etc.); anemia conditions; neurological-related conditions (e.g., ADHD, ADD, anxiety, Asperger's syndrome, autism, chronic fatigue syndrome, depression, etc.); autoimmune-related conditions (e.g., Sprue, AIDS, Sjogren's, Lupus, etc.); endocrine-related conditions (e.g., obesity, Graves' disease, Hashimoto's thyroiditis, metabolic disease, Type I diabetes, Type II diabetes, etc.); Lyme disease conditions; communication-related conditions; sleep-related conditions; pain-related conditions; genetic-related conditions; chronic disease; and/or any other suitable type of conditions. Additionally or alternatively, conditions can include one or more human behavior conditions which can include any one or more of: caffeine consumption, alcohol consumption, other food item consumption, dietary supplement consumption, probiotic-related behaviors (e.g., consumption, avoidance, etc.), other dietary behaviors, habituary behaviors (e.g., smoking; exercise conditions such as low, moderate, and/or extreme exercise conditions; etc.), menopause, other biological processes, social behavior, other behaviors, and/or any other suitable human behavior conditions.

Conditions can include one or more of: diseases, symptoms, causes (e.g., triggers, etc.), disorders, associated risk (e.g., propensity scores, etc.), associated severity, behaviors (e.g., caffeine consumption, habits, diets, etc.), and/or any other suitable aspects associated with conditions. Conditions can be associated with any suitable phenotypes (e.g., phenotypes measurable for a human, animal, plant, fungi body, etc.).

In examples, the condition (e.g., one or more conditions; etc.) can include at least one of a cardiovascular condition (e.g., atherosclerosis; etc.), a renal condition (e.g., renal failure; etc.), a metabolic-related condition (e.g., trimethylaminuria; etc.), and/or a nutrition-related condition (e.g., a weight-related condition; a high blood sugar-related condition; etc.); where the condition can be associated with at least one of TMA, TMAO, and/or derivatives thereof; and where administering to one or more patients can include administering, to the one or more patients with the one or more conditions (e.g., ; etc.), a therapeutically effective amount of one or more compounds (e.g., any suitable compounds in and/or including any suitable combination of compounds from Tables 1-8; etc.) for inhibiting one or more enzymes (e.g., CutC enzymes; CntA enzymes; enzymes associated with the at least one of TMA, TMAO, and/or derivatives thereof; etc.) of microorganisms from at least one of *Firmicutes* (phylum) and/or *Proteobacteria* (phylum).

Additionally or alternatively, data described herein (e.g., binding parameters; interaction parameters; identified compounds; outputs from models and/or experiments; etc.) can be associated with any suitable temporal indicators (e.g., seconds, minutes, hours, days, weeks, time periods, time points, timestamps, etc.) including one or more: temporal indicators indicating when the data was collected, determined, transmitted, received, and/or otherwise processed; temporal indicators providing context to content described by the data; changes in temporal indicators (e.g., data over time; change in data; data patterns; data trends; data extrapolation and/or other prediction; etc.); and/or any other suitable indicators related to time.

Additionally or alternatively, parameters, metrics, inputs, outputs, and/or other suitable data can be associated with value types including any one or more of: scores (e.g., binding parameters; interaction parameters; etc.), binary values (e.g., presence of a target within a microorganism taxon; etc.), classifications (e.g., taxon classifications; etc.), confidence levels, identifiers (e.g., compound identifiers; etc.), values along a spectrum, and/or any other suitable types of values. Any suitable types of data described herein can be used as inputs (e.g., for different models described herein; for portions of embodiments the method 100; etc.), generated as outputs (e.g., of models), and/or manipulated in any suitable manner for any suitable components associated with embodiments of the method 100 and/or system 200.

One or more instances and/or portions of embodiments of the method 100 and/or processes described herein can be performed asynchronously (e.g., sequentially), concurrently (e.g., in parallel; concurrently on different threads for parallel computing to improve system processing ability for screening and/or otherwise determining compounds; etc.), in temporal relation to a trigger event (e.g., performance of a portion of the method 100), and/or in any other suitable order at any suitable time and frequency by and/or using one or more instances of embodiments of the system 200, components, and/or entities described herein.

Embodiments of the system 200 can include any one or more of: compounds and/or pharmaceutically acceptable forms thereof, and/or salts (e.g., pharmaceutically acceptable salts; etc.) thereof; computing systems (e.g., for identifying one or more compounds; etc.); sample handling networks; sequencing systems; and/or any other suitable components. The system 200 and/or portions of the system 200 can entirely or partially be executed by, hosted on, communicate with, and/or otherwise include: a remote computing system (e.g., a server, at least one networked computing system, stateless, stateful; etc.), a local computing system, a user device (e.g., mobile phone device, other mobile device, personal computing device, tablet, wearable, head-mounted wearable computing device, wrist-mounted wearable computing device, etc.), a care provider device, databases, application programming interfaces (APIs) (e.g., for accessing data described herein, etc.) and/or any suitable components. Communication by and/or between any components of the system 200 can include wireless communication (e.g., WiFi, Bluetooth, radiofrequency, Zigbee, Z-wave, etc.), wired communication, and/or any other suitable types of communication. The components of the system 200 can be physically and/or logically integrated in any manner (e.g., with any suitable distributions of functionality across the components, such as in relation to portions of embodiments of the method 100; etc.).

Portions of embodiments of the method 100 and/or system 200 can be performed by any one or more of: first parties; third parties; car providers (e.g., doctors; nurses; etc.); lab technicians; users; compound providers; and/or any suitable entities.

However, embodiments of the method 100 and/or system 200 can be configured in any suitable manner.

2.1 Administering a Compound.

Embodiments of the method 100 can include administering (and/or other suitable provision of; promotion of; etc.) administering one or more compounds (e.g., a therapeutically effective amount of the one or more compounds; etc.) to one or more patients with one or more conditions Silo (e.g., one or more conditions associated with the at least one of TMA, TMAO, and/or derivatives thereof; etc.), which can function to facilitate treatment of one or more patients.

A therapeutically effective amount of the one or more compounds is preferably administered, but any suitable amounts of the one or more compounds can be administered.

The compounds (e.g., drugs; molecules; etc.) preferably affect (e.g., inhibiting; etc.) one or more targets (e.g., CutC enzymes; CntA enzymes; etc.) associated with one or more conditions associated at least one of TMA, TMAO, and/or derivatives thereof, such as for inhibiting production of TMA, TMAO, and/or derivatives thereof (e.g., for preventing, treating, and/or reducing the effect of conditions associated with TMA, TMAO, and/or derivatives thereof; etc.). Additionally or alternatively, the compounds can otherwise affect (e.g., activate, upregulate, downregulate, bind; etc.) the one or more targets, and/or the targets can be associated with any suitable conditions. Compounds can include any suitable combination of (e.g., one or more; combinations; individual molecules and/or compounds; etc.), derivative of, pharmaceutically acceptable form of, and/or any suitable form of compounds included in Tables 1-8.

Compounds can include any suitable pharmaceutically acceptable forms of the compounds, which can include any one or more of: derivatives; pharmaceutically deliverable forms; forms with carriers, agents, supplemental components; salts; and/or any suitable acceptable forms. Compounds can include any suitable salts (e.g., pharmaceutically acceptable salts; etc.) thereof, and/or any suitable forms of the compounds.

Targets (e.g., targets targeted by the one or more compounds; targets causing, contributing to, with therapeutic effect in relation to, correlated with, and/or otherwise associated with one or more conditions etc.) can include any one or more of: CutC enzymes; CntA enzymes; CutD enzymes; CntB enzymes; other enzymes (e.g., associated with at least one of TMA, TMAO, and/or derivatives thereof; etc.); proteins; target markers (e.g., biomarkers; etc.); targets of interest; known or identified targets; unknown or previously unidentified targets; genetic targets; sequences (e.g., amino acid sequences; nucleic acid sequences; etc.); compounds; peptides; carbohydrates; lipids; nucleic acids; cells (e.g., whole cells, etc.); metabolites; natural products; diagnostic biomarkers; prognostic biomarkers; predictive biomarkers; other molecular biomarkers; biological targets; non-biological targets; other molecules (e.g., associated with at least one of TMA, TMAO, and/or derivatives thereof; etc.); and/or any other suitable targets.

Targets are preferably associated with microorganisms (e.g., are from the microorganisms; are produced by the microorganisms; have been found in relation to the microorganisms; are present in the microorganisms; are encoded by genetic sequences, amino acid sequences, and/or other suitable sequences of the microorganisms; etc.) from at least one taxon from a set of microorganism taxa (e.g., from at least one of *Firmicutes* (phylum) and *Proteobacteria* (phylum); etc.). Additionally or alternatively, targets can be associated with microorganisms from any suitable microorganism taxa (e.g., domain, kingdom, phylum, class, order, family, genus, species; etc.) and/or microorganisms associated with any suitable body site including any one or more of gut, skin, nose, mouth, genitals, and/or any suitable body site. Administering a compound can include any one or more of providing, promoting, and/or otherwise administering a compound.

Administering one or more compounds can include administering (e.g., a therapeutically effective amount of; etc.) one or more compounds for inhibiting (and/or otherwise affecting) CutC enzymes, such as CutC enzymes of microorganisms from at least one of *Firmicutes* (phylum), *Proteobacteria* (phylum), and/or other suitable taxa.

Compounds for inhibiting (and/or otherwise affecting) CutC enzymes (e.g., associated with microorganisms from at least one of *Proteobacteria* and *Firmicutes*; etc.) can include one or more 3,3-dimethyl-1-butanol (DMB) analogues (e.g., binding with equal or higher affinity to CutC enzymes than DMB, such as for CutC enzymes belonging to *Proteobacteria* and/or *Firmicutes*; etc.). In examples, DMB can inhibit TMA formation by CutC enzymes (e.g., derived from cultured microbes in a non-lethal way, such as not an antibiotic); can reduce TMAO levels (e.g., in animals with a high choline or carnitine diet; etc.); and/or can bind the active site of CutC enzymes (e.g., with higher affinity than choline, thereby exerting competitive inhibition; etc.). In examples, DMB analogues (and/or compounds generally) can include any one or more compounds included in Table 1.

TABLE 1

Examples of Analogues of DMB that can Bind CutC Enzymes of Microorganisms from Proteobacteria and/or Firmicutes.

| Structure | SMILES code | IUPAC nomenclature | Binding Energy (to CutC enzyme, Proteobacteria | Binding Energy (to CutC enzyme, Firmicutes) |
|---|---|---|---|---|
| 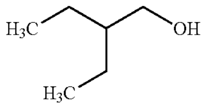 | CCC(CC)CO | 2-Ethyl-1-butanol | −4.9 kcal/mol | |
| 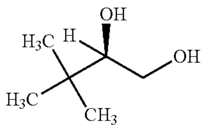 | CC(C)(C)[C@H](CO)O | (2R)-3,3-Dimethyl-1,2-butanediol | −5.5 kcal/mol | −5.2 kcal/mol |
| 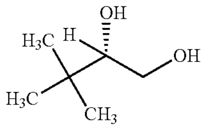 | CC(C)(C)[C@@H](CO)O | (2S)-3,3-Dimethyl-1,2-butanediol | −5.4 kcal/mol | −5.2 kcal/mol |
| 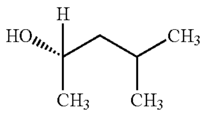 | C[C@@H](CC(C)C)O | (2S)-4-Methyl-2-pentanol | −5.2 kcal/mol | |
| 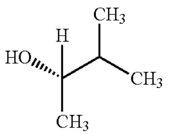 | C[C@@H](C(C)C)O | (2S)-3-Methyl-2-butanol | −4.8 kcal/mol | |
| 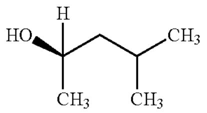 | C[C@H](CC(C)C)O | (2R)-4-Methyl-2-pentanol | −5.0 kcal/mol | |
| 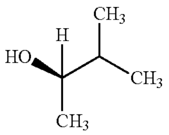 | C[C@H](C(C)C)O | (2R)-3-Methyl-2-butanol | −4.8 kcal/mol | |
| 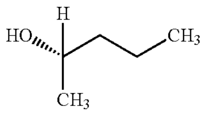 | CCC[C@H](C)O | (2S)-2-Pentanol | −4.8 kcal/mol | |

TABLE 1-continued

Examples of Analogues of DMB that can Bind CutC Enzymes of Microorganisms from Proteobacteria and/or Firmicutes.

| Structure | SMILES code | IUPAC nomencla-ture | Binding Energy (to CutC enzyme, Proteobac-teria | Binding Energy (to CutC enzyme, Firmi-cutes) |
|---|---|---|---|---|
| 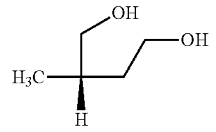 | C[C@@H](CCO)CO | (2S)-2-Methyl-1,4-butanediol | −4.9 kcal/mol | −5.0 kcal/mol |
| 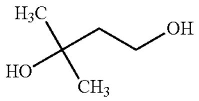 | CC(C)(CCO)O | 2-Methyl-2,4-butanediol | −4.9 kcal/mol | −5.1 kcal/mol |
| 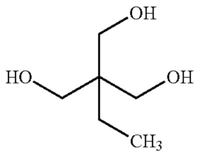 | CCC(CO)(CO)CO | Trimethylol propane | −5.2 kcal/mol | −5.3 kcal/mol |

In an example, administering to the patient with the one or more conditions can include administering, to the patient with the one or more conditions, a therapeutically effective amount of a compound including a 3,3-dimethyl-1-butanol (DMB) analogue including at least one (e.g., any one or more; etc.) of: 2-Ethyl-1-butanol; (2R)-3,3-Dimethyl-1,2-butanediol; (2S)-3,3-Dimethyl-1,2-butanediol; (2S)-4-Methyl-2-pentanol; (2S)-3-Methyl-2-butanol; (2R)-4-Methyl-2-pentanol; (2R)-3-Methyl-2-butanol; (2S)-2-Pentanol; (2S)-2-Methyl-1,4-butanediol; 2-Methyl-2,4-butanediol; Trimethylolpropane; and pharmaceutically acceptable forms thereof (e.g., derivatives thereof; pharmaceutically deliverable forms thereof; etc.); and/or salts (e.g., pharmaceutically acceptable salts; etc.) thereof. However, compounds including a 3,3-dimethyl-1-butanol (DMB) analogue can be configured in any suitable manner, and administering such compounds can be performed in any suitable manner (e.g., for affecting any suitable targets).

Compounds for inhibiting (and/or otherwise affecting) CutC enzymes can include one or more compounds for inhibiting the CutC enzymes of microorganisms from *Firmicutes* (phylum), such as where the one or more compounds (and/or compounds generally) can include any one or more compounds included in Table 2 (e.g., where the compounds can include specificity for CutC enzymes from microorganisms from *Firmicutes*; where the compounds do not bind or bind with lower affinity to CutC enzymes from microorganisms from *Proteobacteria*; where each compound can be representative of a subset of molecules exerting the same binding energy and such as with similar structure to the compound; where the compounds can include higher affinity, as indicated by the binding energy values, than choline or DMB, to the CutC enzymes; etc.).

TABLE 2

Examples of Compounds (e.g., molecules) that can Bind CutC Enzymes of Microorganisms from Firmicutes (e.g., Firmicutes-CoD5P1 CutC Enzyme)

| Structure | SMILES code | IUPAC nomenclature | Binding Energy (to CutC enzyme, Firmicutes) |
|---|---|---|---|
| 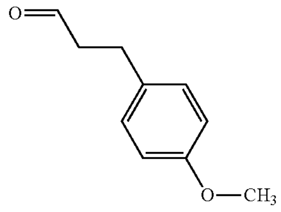 | COc1ccc(cc1)CCC═O | 3-(4-Methoxyphenyl) propanol | −4.9 kcal/mol |

TABLE 2-continued

Examples of Compounds (e.g., molecules) that can Bind CutC Enzymes of Microorganisms from Firmicutes (e.g., Firmicutes-CoD5P1 CutC Enzyme)

| Structure | SMILES code | IUPAC nomenclature | Binding Energy (to CutC enzyme, Firmicutes) |
|---|---|---|---|
| 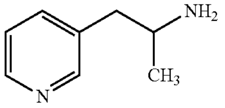 | C[C@H](Cc1cccnc1)[$NH_3$+] | 1-(3-Pyridinyl)-2-propanamine | −5.0 kcal/mol |
| 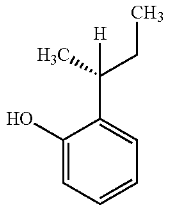 | CC[C@@H](C)c1ccccc1O | 2-[(2R)-2-Butanyl]phenol | −5.2 kcal/mol |
| 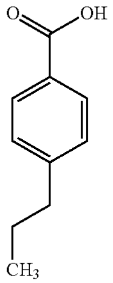 | CCCc1ccc(cc1)C(═O)O | 4-Propylbenzoic acid | −5.3 kcal/mol |
| 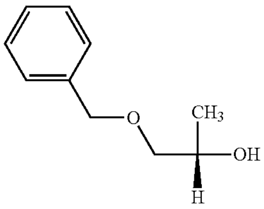 | C[C@@H](COCc1ccccc1)O | (2S)-1-(Benzyloxy)-2-propanol | −5.4 kcal/mol |
| 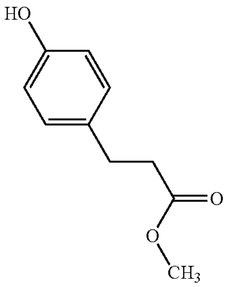 | COC(═O)CCc1ccc(cc1)O | Methyl 3-(4-hydroxyphenyl) propanoate | −5.5 kcal/mol |
| 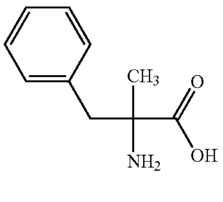 | C[C@@](Cc1ccccc1)(C(═O)O)[$NH_3$+] | α-Methylphenyl-alanine | −5.6 kcal/mol |

TABLE 2-continued

Examples of Compounds (e.g., molecules) that can Bind CutC Enzymes of Microorganisms from Firmicutes (e.g., Firmicutes-CoD5P1 CutC Enzyme)

| Structure | SMILES code | IUPAC nomenclature | Binding Energy (to CutC enzyme, Firmicutes) |
|---|---|---|---|
| 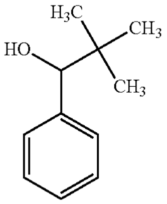 | CC(C)(C)C(c1ccccc1)O | 2,2-Dimethyl-1-phenyl-1-propanol | −5.7 kcal/mol |
| 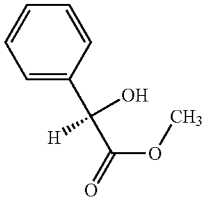 | COC(=O)[C@@H](c1ccccc1)O | Methyl (2R)-hydroxy(phenyl) acetate | −5.8 kcal/mol |
| 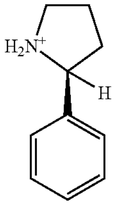 [SMILES: c1ccc([C@@H]2CCC[NH2+]2)cc1] | c1ccc(cc1)[C@@H]1CCC[NH2+]1 | (2S)-2-Phenylpyrrolidinium | −5.9 kcal/mol |
| 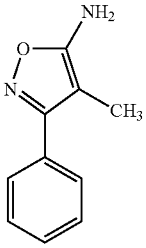 | Cc1c(noc1N)c1ccccc1 | 4-Methyl-3-phenyl-1,2-oxazol-5-amine | −6.0 kcal/mol |
| 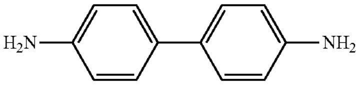 [SMILES: Nc1ccc(-c2ccc(N)cc2)cc1] | c1cc(ccc1c1ccc(cc1)N)N | 4,4'-Biphenyldiamine | −6.1 kcal/mol |
| 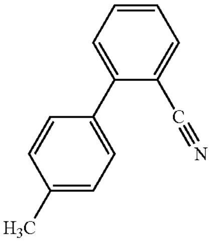 | Cc1ccc(cc1)c1ccccc1C#N | 4'-Methyl-2-biphenylcarbonitrile | −6.2 kcal/mol |
| 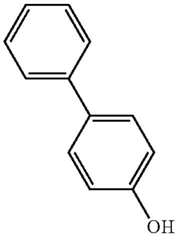 [SMILES: Oc1ccc(-c2ccccc2)cc1] | c1ccc(cc1)c1ccc(cc1)O | 4-Biphenylol | −6.3 kcal/mol |

TABLE 2-continued

| Structure | SMILES code | IUPAC nomenclature | Binding Energy (to CutC enzyme, Firmicutes) |
|---|---|---|---|
| Examples of Compounds (e.g., molecules) that can Bind CutC Enzymes of Microorganisms from Firmicutes (e.g., Firmicutes-CoD5P1 CutC Enzyme) | | | |
| 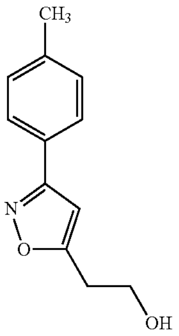 | Cc1ccc(cc1)c1cc(on1)CCO | 2-[3-(4-Methylphenyl)-1,2-oxazol-5-yl]ethanol | −6.4 kcal/mol |
| 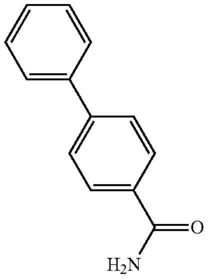 [SMILES: NC(=O)c1ccc(-c2ccccc2)cc1] | c1ccc(cc1)c1ccc(cc1)C(=O)N | 4-Biphenylcarboxamide | −6.5 kcal/mol |
| 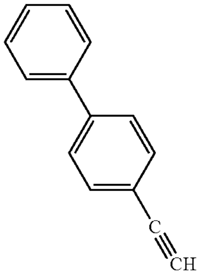 | C#Cc1ccc(cc1)c1ccccc1 | 4-Ethynylbiphenyl | −6.6 kcal/mol |
| 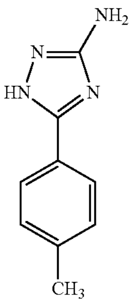 | Cc1ccc(cc1)c1nc([nH]n1)N | 5-(4-Methylphenyl)-1H-1,2,4-triazol-3-amine | −6.7 kcal/mol |

TABLE 2-continued

Examples of Compounds (e.g., molecules) that can Bind CutC Enzymes of Microorganisms from Firmicutes (e.g., Firmicutes-CoD5P1 CutC Enzyme)

| Structure | SMILES code | IUPAC nomenclature | Binding Energy (to CutC enzyme, Firmicutes) |
|---|---|---|---|
| 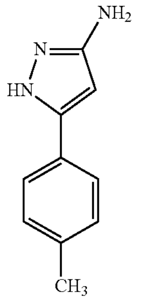 | Cc1ccc(cc1)c1cc([nH]n1)N | 5-(4-Methylphenyl)-1H-pyrazol-3-amine | −6.8 kcal/mol |
| 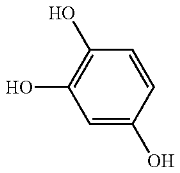 | c1cc(c(cc1O)O)O | 4-Hydroxycatechol | −6.9 kcal/mol |
| 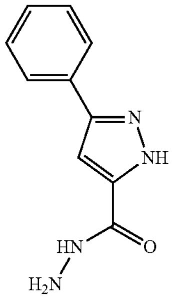 [SMILES: NNC(=O)c1cc(-c2ccccc2)n[nH]1] | c1ccc(cc1)c1cc(n[nH]1)C(=O)NN | 3-Phenyl-1H-pyrazole-5-carbohydrazide | −7.0 kcal/mol |
| 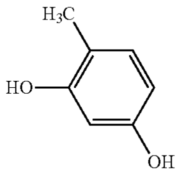 | Cc1ccc(cc1O)O | 4-Methyl-1,3-benzenediol | −7.1 kcal/mol |

In an example, administering to the patient with the one or more conditions can include administering, to the patient with the one or more conditions, a therapeutically effective amount of a compound for inhibiting the CutC enzymes of the microorganisms from *Firmicutes* (phylum), where the compound includes at least one (e.g., any one or more; etc.) of: 3-(4-Methoxyphenyl)propanal; 1-(3-Pyridinyl)-2-propanamine; 2-[(2R)-2-Butanyl]phenol; 4-Propylbenzoic acid; (2S)-1-(Benzyloxy)-2-propanol; Methyl 3-(4-hydroxyphenyl)propanoate; α-Methylphenylalanine; 2,2-Dimethyl-1-phenyl-1-propanol; Methyl (2R)-hydroxy(phenyl)acetate; (2S)-2-Phenylpyrrolidinium; 4-Methyl-3-phenyl-1,2-oxazol-5-amine; 4,4'-Biphenyldiamine; 4'-Methyl-2-biphenylcarbonitrile; 4-Biphenylol; 2-[3-(4-Methylphenyl)-1,2-oxazol-5-yl]ethanol; 4-Biphenylcarboxamide; 4-Ethynylbiphenyl; 5-(4-Methylphenyl)-1H-1,2,4-triazol-3-amine; 5-(4-Methylphenyl)-1H-pyrazol-3-amine; 4-Hydroxycatechol; 3-Phenyl-1H-pyrazole-5-carbohydrazide; 4-Methyl-1,3-benzenediol; and pharmaceutically acceptable forms thereof (e.g., derivatives thereof; pharmaceutically deliverable forms thereof; etc.); and/or salts (e.g., pharmaceutically acceptable salts; etc.) thereof. However, compounds for inhibiting CutC enzymes of microorganisms from *Firmicutes* (phylum) can be configured in any suitable manner, and administering such compounds can be performed in any suitable manner (e.g., for affecting any suitable targets).

Compounds for inhibiting (and/or otherwise affecting) CutC enzymes can include one or more compounds for inhibiting the CutC enzymes of microorganisms from *Proteobacteria* (phylum), such as where the one or more compounds (and/or compounds generally) can include any one or more compounds included in Table 3 (e.g., where the compounds can include specificity for CutC enzymes from microorganisms from *Proteobacteria*; where the compounds do not bind or bind with lower affinity to CutC enzymes from microorganisms from *Firmicutes*; where each compound can be representative of a subset of molecules exerting the same binding energy and such as with similar structure to the compound; where the compounds can include higher affinity, as indicated by the binding energy values, than choline or DMB, to the CutC enzymes; etc.).

TABLE 3

Examples of Compounds (e.g, molecules) that can Bind CutC Enzymes of Microorganisms from Proteobacteria (e.g., Proteobacteria-$B_4$EYG1 CutC Enzyme)

| Structure | SMILES code | IUPAC nomenclature | Binding Energy (to CutC enzyme, Proteobacteria) |
|---|---|---|---|
| 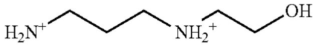 | C(C[NH3+])C[NH2+]CCO | N-(2-Hydroxyethyl)-1,3-propanediaminium | −4.8 kcal/mol |
| 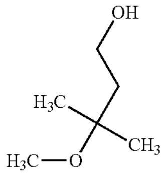 | CC(C)(CCO)OC | 3-Methoxy-3-methylbutanol | −4.9 kcal/mol |
| 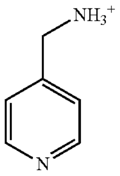 | c1cnccc1C[NH3+] | 4-Pyridinylmethan-aminium | −5.0 kcal/mol |
| 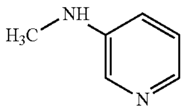 | CNc1cccnc1 | N-Methyl-3-pyridinamine | −5.1 kcal/mol |
| 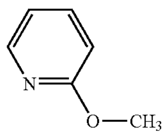 | COc1ccccn1 | 2-Methoxypyridine | −5.2 kcal/mol |
| 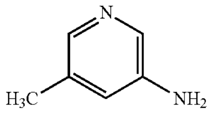 | Cc1cc(cnc1)N | 5-Methyl-3-pyridinamine | −5.3 kcal/mol |
| 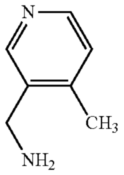 | Cc1ccncc1C[NH3+] | 1-(4-Methyl-3-pyridinyl)rnethan amine | −5.4 kcal/mol |
| 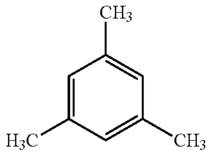 | Cc1cc(cc(c1)C)C | Mesitylene | −5.5 kcal/mol |
| 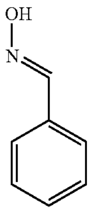 | c1ccc(cc1)/C=NO | (E)-Benzaldoxime | −5.6 kcal/mol |

TABLE 3-continued

Examples of Compounds (e.g, molecules) that can Bind CutC Enzymes of Microorganisms from Proteobacteria (e.g., Proteobacteria-$B_4$EYG1 CutC Enzyme)

| Structure | SMILES code | IUPAC nomenclature | Binding Energy (to CutC enzyme, Proteobacteria) |
|---|---|---|---|
| 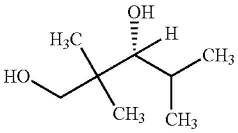 | CC(C)[C@H](C(C)(C)CO)O | (3R)-2,2,4-Trimethyl-1,3-pentanediol | −5.7 kcal/mol |
| 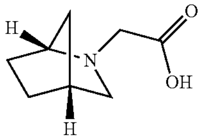 [SMILES: O=C(O)CN1C[C@@H]2CC[C@@H]1C2] | C1C[C@@H]2C[C@H]1C[N@@H+]2CC(=O)O | (1R,4R)-2-Azabicyclo[2.2.1]hept-2-ylacetic acid | −5.8 kcal/mol |
| 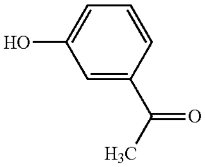 | CC(=O)c1cccc(c1)O | 3-ACETYLPHENOL | −5.9 kcal/mol |
| 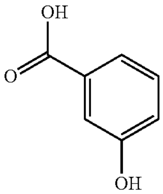 | c1cc(cc(c1)O)C(=O)O | 3-Hydroxybenzoicacid | −6.0 kcal/mol |
| 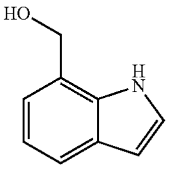 | c1cc2cc[nH]c2c(c1)CO | 1H-Indol-7-ylmethanol | −6.1 kcal/mol |
| 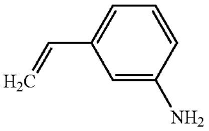 | C=Cc1cccc(c1)N | 3-Vinylaniline | −6.2 kcal/mol |
| 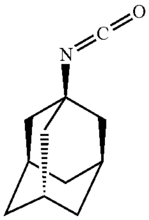 [SMILES: O=C=N[C@]12C[C@H]3C[C@H](C[C@H](C3)C1)C2] | C1[C@H]2C[C@H]3C[C@@H]1C[C@@](C2)(C3)N=C=O | (3s,5s,7s)-1-Isocyanato-adamantane | −6.3 kcal/mol |
| 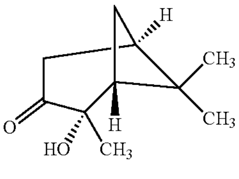 | C[C@@]1([C@@H]2C[C@@H](C2(C)C)CC1=O)O | (1R,2S,5R)-2-Hydroxy-2,6,6-trimethylbicyclo[3.1.1]heptan-3-one | −64 kcal/mol |

TABLE 3-continued

Examples of Compounds (e.g, molecules) that can Bind CutC Enzymes of Microorganisms from Proteobacteria (e.g., Proteobacteria-$B_4$EYG1 CutC Enzyme)

| Structure | SMILES code | IUPAC nomenclature | Binding Energy (to CutC enzyme, Proteobacteria) |
|---|---|---|---|
| 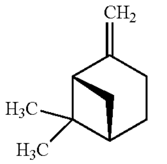 | CC1([C@H]2CCC(═C)[C@@H]1C2)C | (-)-β-Pinene | −6.5 kcal/mol |
| 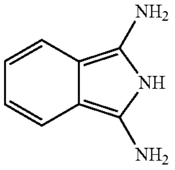 [SMILES: Nc1[nH]c(N)c2ccccc12] | c1ccc2c(c1)c([nH]c2N)N | 2H-Isoindole-1,3-diamine | −6.6 kcal/mol |
| 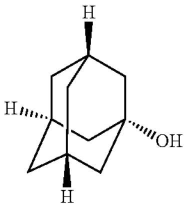 [SMILES: O[C@]12C[C@H]3C[C@H](C[C@H](C3)C1)C2] | C1[C@H]2C[C@H]3C[C@@H]1C[C@@(C2)(C3)O | (3S,5S,7S)-1-Adamantanol | −6.7 kCa1/11101 |
| 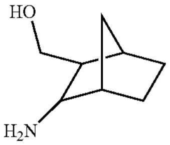 | C1[C@H]2C[C@@H]1[C@H]([C@H]2[$NH_3$+])CO | (3-Aminobicyclo[2.2.1hept-2-yl)methanol | −6.8 kcal/mol |
| 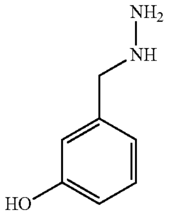 | c1cc(cc(c1)O)CN[$NH_3$+] | 3-(Hydrazinomethyl)phenol | −6.9 kcal/mol |
| 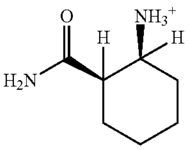 | C1CC[C@@H]([C@@H](C1)C(═O)N)[$NH_3$+] | (1S,2R)-2-Carbamoylcyclo-hexanaminium | −7.0 kcal/mol |
| 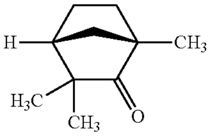 | C[C@]12CC[C@H](C1)C(C2═O)(C)C | (1S,4R)-1,3,3-Trimethylbicyclo[2.2.1]heptan-2-one | −7.1 kcal/mol |
| 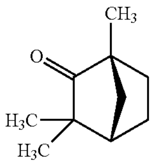 | C[C@@]12CC[C@@H](C1)C(C2═O)(C)C | (1R,4S)-1,3,3-Trimethylbicyclo[2.2.1]heptan-2-one | −7.4 kcal/mol |

In an example, administering to the patient with the one or more conditions can include administering, to the patient with the one or more conditions, a therapeutically effective amount of a compound for inhibiting the CutC enzymes of the microorganisms from *Proteobacteria* (phylum), where the compound includes at least one (e.g., any one or more; etc.) of: N-(2-Hydroxyethyl)-1,3-propanediaminium; 3-Methoxy-3-methylbutanol; 4-Pyridinylmethanaminium; N-Methyl-3-pyridinamine; 2-Methoxypyridine; 5-Methyl-3-pyridinamine; 1-(4-Methyl-3-pyridinyl)methanamine; Mesitylene; (E)-Benzaldoxime' (3R)-2,2,4-Trimethyl-1,3-pentanediol; (1R,4R)-2-Azabicyclo[2.2.1]hept-2-ylacetic acid; 3-ACETYLPHENOL; 3-Hydroxybenzoicacid; 1H-Indol-7-ylmethanol; 3-Vinylaniline; (3s,5s,7s)-1-Isocyanato-adamantane; 2S,5R)-2-Hydroxy-2,6,6-trimethylbicyclo[3.1.1]heptan-3-one; (−)-β-Pinene; 2H-Isoindole-1,3-diamine; (3s,5s,7s)-1-Adamantanol; (3-Aminobicyclo[2.2.1]hept-2-yl)methanol; 3-(Hydrazinomethyl)phenol; (1S,2R)-2-Carbamoylcyclohexanaminium; (1S,4R)-1,3,3-Trimethylbicyclo[2.2.1]heptan-2-one; (1R,4S)-1,3,3-Trimethylbicyclo[2.2.1]heptan-2-one; and pharmaceutically acceptable forms thereof (e.g., derivatives thereof; pharmaceutically deliverable forms thereof; etc.); and/or salts (e.g., pharmaceutically acceptable salts; etc.) thereof. However, compounds for inhibiting CutC enzymes of microorganisms from *Proteobacteria* (phylum) can be configured in any suitable manner, and administering such compounds can be performed in any suitable manner (e.g., for affecting any suitable targets).

Compounds for inhibiting (and/or otherwise affecting) CutC enzymes can include one or more compounds for inhibiting the CutC enzymes of microorganisms from *Firmicutes* (phylum) and *Proteobacteria* (phylum) (e.g., inhibiting CutC enzymes of first microorganisms from *Firmicutes* as well as CutC enzymes of second microorganisms from *Proteobacteria*, etc.), such as where the one or more compounds (and/or compounds generally) can include any one or more compounds included in Table 4 (e.g., compounds binding CutC enzymes associated with *Firmicutes*, and binding CutC enzymes associated with *Proteobacteria*; such as where the compounds can inhibit products of TMA by CutC in a set of microorganisms across different taxa, such as across *Firmicutes* and *Proteobacteria*; where each compound can be representative of a subset of molecules exerting the same binding energy and such as with similar structure to the compound; where the compounds can include higher affinity, as indicated by the binding energy values, than choline or DMB, to the CutC enzymes; etc.).

TABLE 4

Examples of Compounds (e.g., molecules) that can Bind CutC Enzymes of Microorganisms from Proteobacteria and Firmicutes

| Structure | SMILES code | IUPAC nomenclature | Binding Energy (to CutC enzyme, Proteobacteria) | Binding Energy (to CutC enzyme, Firmicutes) |
|---|---|---|---|---|
| 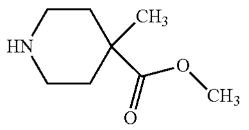 | CC1(CC[NH2+CC1)C(=O)OC | Methyl 4-methyl-4-piperidine-carboxylate | −4.8 kcal/mol | −4.8 kcal/mol |
| 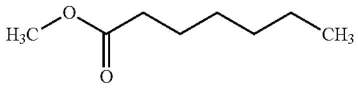 | CCCCCCC(=O)O | Methyl heptanoate | −4.9 kcal/mol | −4.9 kcal/mol |
| 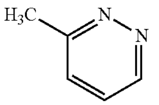 | Cc1cccnn1 | 3-Methyl-pyridazine | −5.0 kcal/mol | −5.0 kcal/mol |
| 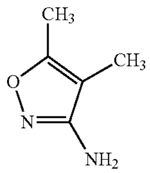 | Cc1c(onc1N)C | 4,5-Dimethyl-1,2-oxazol-3-amine | −5.1 kcal/mol | −5.1 kcal/mol |
| 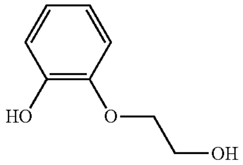 [SMILES: OCCOc1ccccc1O] | c1ccc(c(c1)O)OCCO | 2-(2-Hydroxyethoxy) phenol | −5.2 kcal/mol | −5.2 kcal/mol |

TABLE 4-continued

Examples of Compounds (e.g., molecules) that can Bind CutC Enzymes of Microorganisms from Proteobacteria and Firmicutes

| Structure | SMILES code | IUPAC nomenclature | Binding Energy (to CutC enzyme, Proteobacteria) | Binding Energy (to CutC enzyme, Firmicutes) |
|---|---|---|---|---|
| 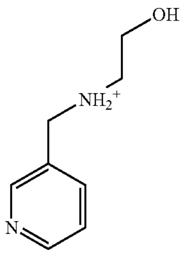 [SMILES: OCC[NH2+]Cc1cccnc1] | c1cc(cnc1)C[NH2+]CCO | 2-Hydroxy-N-(3-pyridinyl-methyl) ethanaminium | −5.3 kcal/mol | −5.3 kcal/mol |
| 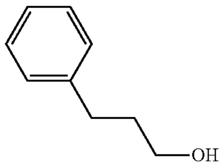 | c1ccc(cci)CCCO | 3-Phenyl-1-propanol | −5.4 kcal/mol | −5.4 kcal/mol |
| 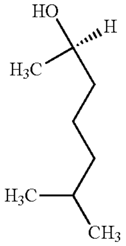 | C[C@H](CCCC(C)C)O | (2R)-6-Methyl-2-heptanol | −5.5 kcal/mol | −5.5 kcal/mol |
| 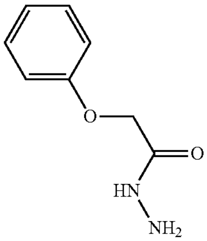 [SMILES: NNC(=O)COc1ccccc1] | c1ccc(cc1)OCC(═O)NN | 2-Phenoxyaceto-hydr azide | −5.6 kcal/mol | −5.6 kcal/mol |
| 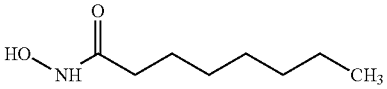 | CCCCCCCC(═O)NO | N-Hydroxy-octanamid | −5.7 kcal/mol | −5.7 kcal/mol |
| 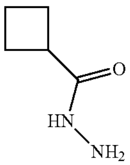 | C1CC(C1)C(═O)NN | Cyclobutane-carbohydrazide | −5.8 kcal/mol | −5.8 kcal/mol |
| 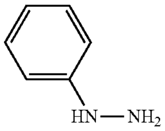 | c1ccc(cc1)NN | Phenylhydrazine | −5.9 kcal/mol | −5.9 kcal/mol |

TABLE 4-continued

Examples of Compounds (e.g., molecules) that can Bind CutC Enzymes of Microorganisms from Proteobacteria and Firmicutes

| Structure | SMILES code | IUPAC nomenclature | Binding Energy (to CutC enzyme, Proteobacteria) | Binding Energy (to CutC enzyme, Firmicutes) |
|---|---|---|---|---|
| 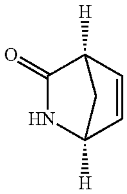 | C1[C@@H]2C═C[C@H]1NC2═O | (1S,4R)-2-Azabicyclo[2.2.1]hept-5-en-3-one | −6.o kcal/mol | −6.0 kcal/mol |
| 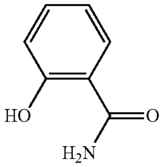 | c1ccc(c(c1)C(═O)N)O | salicylamide | −6.1 kcal/mol | −6.1 kcal/mol |
| 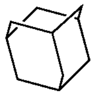 | C1[C@@H]2C[C@@H]3C[C@H]1C[C@H](C2)C3 | Adamantane | −6.2 kcal/mol | −6.2 kcal/mol |
| 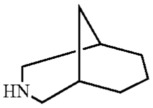 | C1C[C@@H]2C[C@H]C1)C[NH2+]C2 | 3-Azabicyclo[3.3.1]nonane | −6.4 kcal/mol | −6.4 kcal/mol |
| 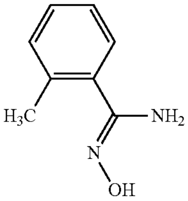 | Cc1ccccc1/C(═N/O)/N | N-Hydroxy-2-methyl-benzene-carbox-imidamide | −6.5 kcal/mol | −4.9 kcal/mol |
| 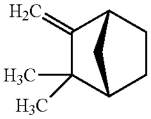 | CC1([C@H]2CC[C@H](C2)C1═C)C | (−)-camphene | −6.6 kcal/mol | −5.4 kcal/mol |

TABLE 4-continued

Examples of Compounds (e.g., molecules) that can Bind CutC Enzymes of Microorganisms from Proteobacteria and Firmicutes

| Structure | SMILES code | IUPAC nomenclature | Binding Energy (to CutC enzyme, Proteobacteria) | Binding Energy (to CutC enzyme, Firmicutes) |
|---|---|---|---|---|
| 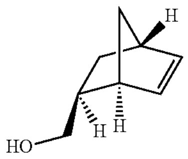 | C1[C@H]2C[C@@H]([C@@H]1C=C2)CO | (1S,2S,4S)-Bicyclo[2.2.1]hept-5-en-2-ylmethanol | −6.7 kcal/mol | −6.1 kcal/mol |
| 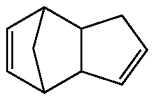 | C1C=C[C@H]2[C@H]([C@H]1C[C@@H]2C=C1 | Dicyclopentadiene | −6.8 kcal/mol | −5.0 kcal/mol |
| 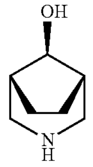 | C1C[C@H]2C[NH2+]C[C@@H]1[C@@H]2O | (8-anti)-3-Azabicyclo[3.2.1]octan-8-ol | −5.8 kcal/mol | −6.9 kcal/mol |
| 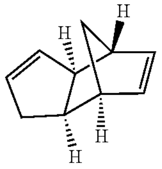 | C1C=C[C@@H]2[C@H]1[C@H]1C[C@@H]2C=C1 | (1R,2S,6R,7S)-Tricyclo[5.2.1.02,6]deca-3,8-diene | −7.0 kcal/mol | −6.0 kcal/mol |

In an example, administering to the patient with the one or more conditions can include administering, to the patient with the one or more conditions, a therapeutically effective amount of a compound for inhibiting the CutC enzymes of the microorganisms from *Firmicutes* (phylum) and *Proteobacteria* (phylum), where the compound includes at least one (e.g., any one or more; etc.) of: Methyl 4-methyl-4-piperidinecarboxylate; Methyl heptanoate; 3-Methylpyridazine; 4,5-Dimethyl-1,2-oxazol-3-amine; 2-(2-Hydroxyethoxy)phenol; 2-Hydroxy-N-(3 -pyridinylmethyl) ethanaminium; 3-Phenyl-1-propanol; (2R)-6-Methyl-2-heptanol; 2-Phenoxyacetohydrazide; N-Hydroxyoctanamid; Cyclobutanecarbohydrazide; Phenylhydrazine; (1S,4R)-2-Azabicyclo[2.2.1]hept-5-en-3-one; salicylamide; Adamantane; 3-Azabicyclo[3.3.1]nonane; N-Hydroxy-2-methylbenzenecarboximidamide; (−)-camphene; (1S,2S,4S)-Bicyclo[2.2.1]hept-5-en-2-ylmethanol; Dicyclopentadiene; (8-anti)-3-Azabicyclo[3.2.1]octan-8-ol; (1R,2S,6R,7S)-Tricyclo[5.2.1.02,6]deca-3,8-diene; and pharmaceutically acceptable forms thereof (e.g., derivatives thereof; pharmaceutically deliverable forms thereof; etc.); and/or salts (e.g., pharmaceutically acceptable salts; etc.) thereof. In an example, compounds including different binding affinities (and/or other suitable interaction parameters) to CutC enzymes depending on the association of the CutC enzyme to a given taxon (e.g., CutC enzymes of microorganisms from *Proteobacteria*; CutC enzymes of microorganisms from *Firmicutes*; etc.), and/or compounds with different affinities generally, can enable different applications, such as where a compound with high affinity can exert an irreversible inhibition on the CutC enzyme. However, compounds for inhibiting CutC enzymes of microorganisms from *Firmicutes* (phylum) and *Proteobacteria* (phylum) can be configured in any suitable manner, and administering such compounds can be performed in any suitable manner (e.g., for affecting any suitable targets).

Administering one or more compounds can include administering (e.g., a therapeutically effective amount of; etc.) one or more compounds for inhibiting (and/or otherwise affecting) CntA enzymes, such as CntA enzymes of microorganisms from at least one of *Firmicutes* (phylum), *Proteobacteria* (phylum), and/or other suitable taxa. In examples, L-carnitine (e.g., a substrate for CntA enzymes; etc.) can facilitate the production of TMA, TMAO, and/or derivatives thereof through binding to an active site on CntA enzymes, and where L-carnitine can be associated with (e.g., cause, correlated with, influence, etc.) metabolic-related conditions, nutritional-related conditions (e.g., weight-related conditions; high blood sugar-related conditions; etc.), and/or other suitable conditions, such as where compounds inhibiting (and/or otherwise affecting) CntA enzymes can decrease the effect of L-carnitine and/or CntA enzymes in relation to the one or more conditions.

Compounds for inhibiting (and/or otherwise affecting) CntA enzymes (e.g., associated with microorganisms from at least one of *Proteobacteria* and *Firmicutes*; etc.) can include one or more L-carnitine analogues (e.g., binding with equal or higher affinity to CntA enzymes than L-carnitine, such as for CntA enzymes belonging to *Proteobacteria* and/or *Firmicutes*; etc.). In examples, the L-carnitine analogues and/or other suitable compounds can bind to CntA enzymes to competitively inhibit the binding of L-carnitine to the CntA enzymes (e.g., where the substrate and inhibitor cannot bind the active site simultaneously; where the competitive inhibition can facilitate decrease in production of TMA, TMAO, and/or derivatives thereof; etc.). In examples, L-carnitine analogues (and/or compounds generally) can include any one or more compounds included in Table 5.

TABLE 5

Examples of Analogues of L-carnitine that can Bind CntA Enzymes of Microorganisms from Proteobacteria and/or Firmicutes.

| Structure | SMILES code | IUPAC nomenclature | Binding Energy (to CntA enzyme, Proteobacteria) | Binding Energy (to CntA enzyme, Firmicutes) |
|---|---|---|---|---|
| 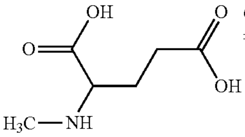 | C[NH2+][C@@H](CCC(=O)O)C(=O)O | N-Methylglutamic acid | | −4.9 kcal/mol |
| 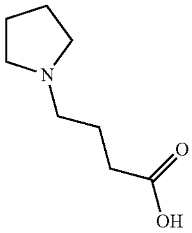 [SMILES: O=C(O)CCCN1CCCC1] | C1CC[NH+](C1)CCCC(=O)O | 4-(1-Pyrrolidinyl) butanoic acid | | −5.1 kcal/mol |
| 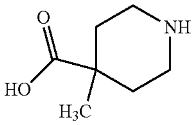 | CC1(CC[NH2+]CC1)C(=O)O | 4-Methyl-4-piperidine carboxylic acid | −4.7 kcal/mol | −5.0 kcal/mol |
| 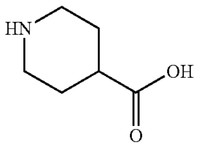 | C1C[NH2+]CCC1C(=O)O | Isonipecotic acid | | −4.9 kcal/mol |

etc.) thereof. However, compounds including an L-carnitine analogue can be configured in any suitable manner, and administering such compounds can be performed in any suitable manner (e.g., for affecting any suitable targets).

Compounds for inhibiting (and/or otherwise affecting) CntA enzymes can include one or more compounds for inhibiting the CntA enzymes of microorganisms from *Firmicutes* (phylum), such as where the one or more compounds (and/or compounds generally) can include any one or more compounds included in Table 6 (e.g., where the compounds can include specificity for CntA enzymes from microorganisms from *Firmicutes*; where the compounds do not bind or bind with lower affinity to CntA enzymes from microorganisms from *Proteobacteria*; where each compound can be representative of a subset of molecules exerting the same binding energy and such as with similar structure to the compound; where the compounds can include higher affinity, as indicated by the binding energy values, than L-carnitine, to the CntA enzymes; etc.).

In an example, administering to the patient with the one or more conditions can include administering, to the patient with the one or more conditions, a therapeutically effective amount of a compound including an L-carnitine analogue including at least one (e.g., any one or more; etc.) of: N-Methylglutamic acid; 4-(1-Pyrrolidinyl)butanoic acid; 4-Methyl-4-piperidinecarboxylic acid; Isonipecotic acid; and pharmaceutically acceptable forms thereof (e.g., derivatives thereof; pharmaceutically deliverable forms thereof; etc.); and/or salts (e.g., pharmaceutically acceptable salts;

TABLE 6

Examples of Compounds (e.g., molecules) that can Bind CntA Enzymes of Microorganisms from Firmicutes (e.g., Firmicutes-$J_3B_3E2$ CntA Enzyme)

| Structure | SMILES code | IUPAC nomenclature | Binding Energy (to CntA enzyme, Firmicutes) |
|---|---|---|---|
| 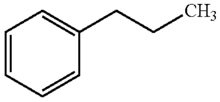 | CCCc1ccccc1 | N-propylbenzene | −5.8 kcal/mol |
| 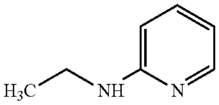 | CCNc1cccc[nH+]1 | N-Ethyl-2-pyridinamine | −5.7 kcal/mol |
| 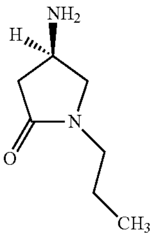 | CCCN1C[C@H](CC1=O)[$NH_3$+] | (4R)-4-Amino-1-propyl-2-pyrrolidinone | −5.6 kcal/mol |
| 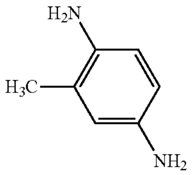 | Cc1cc(ccc1N)N | 2,5-Diaminotoluene | −5.5 kcal/mol |
| 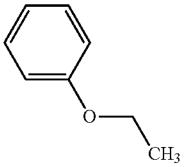 | CCOc1ccccc1 | Ethyl phenyl ether | −5.4 kcal/mol |
| 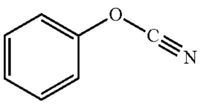 | c1ccc(cc1)OC#N | Phenylcyanate | −5.3 kcal/mol |
| 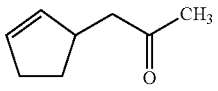 | CC(=O)C[C@@H]1CCC=C1 | 1-(2-Cyclopenten-1-yl)acetone | −5.2 kcal/mol |
| 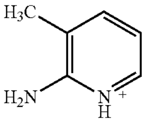 | Cc1ccc[nH+]c1N | 2-Amino-3-methylpyridinium | −5.1 kcal/mol |
| 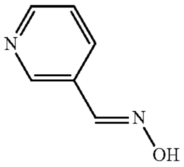 | c1cc(cnc1)/C=N/O | E-pyridine-3-aldoxime | −5.0 kcal/mol |

TABLE 6-continued

| Examples of Compounds (e.g., molecules) that can Bind CntA Enzymes of Microorganisms from Firmicutes (e.g., Firmicutes-$J_3B_3E2$ CntA Enzyme) | | | |
|---|---|---|---|
| Structure | SMILES code | IUPAC nomenclature | Binding Energy (to CntA enzyme, Firmicutes) |
| 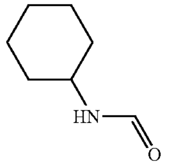 | C1CCC(CC1)NC=O | N-Cyclohexyl-formamide | −4.9 kcal/mol |
| 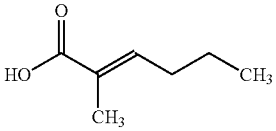 | CCC/C=C(\C)/C(=O)O | 2-Methyl-2-hexenoic acid | −4.8 kcal/mol |
| 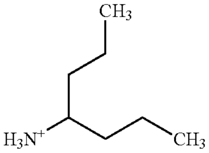 | CCCC(CCC)[$NH_3$+] | 4-Heptanaminium | −4.7 kcal mol |

In an example, administering to the patient with the one or more conditions can include administering, to the patient with the one or more conditions, a therapeutically effective amount of a compound for inhibiting the CntA enzymes of the microorganisms from *Firmicutes* (phylum), where the compound includes at least one (e.g., any one or more; etc.) of: N-propylbenzene; N-Ethyl-2-pyridinamine; (4R)-4-Amino-1-propyl-2-pyrrolidinone; 2,5-Diaminotoluene; Ethyl phenyl ether; Phenylcyanate; 1-(2-Cyclopenten-1-yl) acetone; 2-Amino-3-methylpyridinium; E-pyridine-3-aldoxime; N-Cyclohexylformamide; 2-Methyl-2-hexenoic acid; 4 -Heptanaminium; and pharmaceutically acceptable forms thereof (e.g., derivatives thereof; pharmaceutically deliverable forms thereof; etc.); and/or salts (e.g., pharmaceutically acceptable salts; etc.) thereof. However, compounds for inhibiting CntA enzymes of microorganisms from *Firmicutes* (phylum) can be configured in any suitable manner, and administering such compounds can be performed in any suitable manner (e.g., for affecting any suitable targets).

Compounds for inhibiting (and/or otherwise affecting) CntA enzymes can include one or more compounds for inhibiting the CntA enzymes of microorganisms from *Proteobacteria* (phylum), such as where the one or more compounds (and/or compounds generally) can include any one or more compounds included in Table 7 (e.g., where the compounds can include specificity for CntA enzymes from microorganisms from *Proteobacteria*; where the compounds do not bind or bind with lower affinity to CntA enzymes from microorganisms from *Firmicutes*; where each compound can be representative of a subset of molecules exerting the same binding energy and such as with similar structure to the compound; where the compounds can include higher affinity, as indicated by the binding energy values, than L-carnitine, to the CntA enzymes; etc.).

TABLE 7

| Examples of Compounds (e.g., molecules) that can Bind CntA Enzymes of Microorganisms from Proteobacteria (e.g., Proteobacteria-L1LUC$_3$CntA Enzyme) | | | |
|---|---|---|---|
| Structure | SMILES code | IUPAC nomenclature | Binding Energy (to CntA enzyme, Proteobacteria) |
| 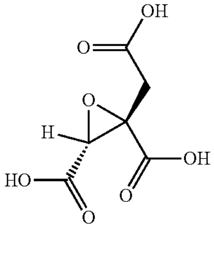 [SMILES: O=C(O)C[C@]1(C(=O)O)O[C@H]1C(=O)O] | C(C(=O)O)[C@]1([C@@H](O1)C(=O)O)C(=O)O | 3,4-Anhydro-3-carboxy-2-deoxy-L-threo-pentaric acid | −4.8 kcal/mol |

TABLE 7-continued

Examples of Compounds (e.g., molecules) that can Bind CntA Enzymes of Microorganisms from Proteobacteria (e.g., Proteobacteria-L1LUC$_3$CntA Enzyme)

| Structure | SMILES code | IUPAC nomenclature | Binding Energy (to CntA enzyme, Proteobacteria) |
|---|---|---|---|
| 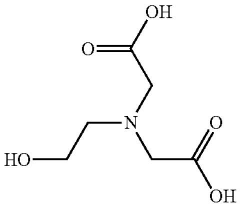 [SMILES: O=C(O)CN(CCO)CC(=O)O] | C(CO)[NH+](CC(=O)O)CC(=O)O | 2,2'-[(2-Hydroxyethyl)imino]diacetic acid | −4.6 kcal/mol |
| 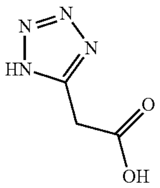 | C(c1nn[nH]n1)C(=O)O | 1H-Tetrazol-5-ylacetic acid | −4.5 kcal/mol |
| 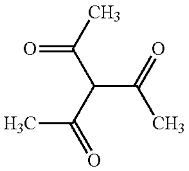 | CC(=O)C(C(=O)C)C(=O)C | Diacetylacetone | −4.4 kcal/mol |
| 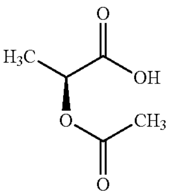 | C[C@@H](C(=O)O)OC(=O)C | (2S)-2-Acetoxypropanoic acid | −4.3 kcal/mol |

In an example, administering to the patient with the one or more conditions can include administering, to the patient with the one or more conditions, a therapeutically effective amount of a compound for inhibiting the CntA enzymes of the microorganisms from *Proteobacteria* (phylum), where the compound includes at least one (e.g., any one or more; etc.) of: 3,4-Anhydro-3-carboxy-2-deoxy-L-threo-pentaric acid; 2,2'-[(2-Hydroxyethyl)imino]diacetic acid; 1H-Tetrazol-5-ylacetic acid; Diacetylacetone; (2S)-2-Acetoxypropanoic acid; and pharmaceutically acceptable forms thereof (e.g., derivatives thereof; pharmaceutically deliverable forms thereof; etc.); and/or salts (e.g., pharmaceutically acceptable salts; etc.) thereof. However, compounds for inhibiting CntA enzymes of microorganisms from *Proteobacteria* (phylum) can be configured in any suitable manner, and administering such compounds can be performed in any suitable manner (e.g., for affecting any suitable targets).

Compounds for inhibiting (and/or otherwise affecting) CntA enzymes can include one or more compounds for inhibiting the CntA enzymes of microorganisms from *Firmicutes* (phylum) and *Proteobacteria* (phylum) (e.g., inhibiting CntA enzymes of first microorganisms from *Firmicutes* as well as CntA enzymes of second microorganisms from *Proteobacteria*, etc.), such as where the one or more compounds (and/or compounds generally) can include any one or more compounds included in Table 8 (e.g., compounds binding CntA enzymes associated with *Firmicutes*, and binding CntA enzymes associated with *Proteobacteria*; such as where the compounds can inhibit products of TMA by CntA in a set of microorganisms across different taxa, such as across *Firmicutes* and *Proteobacteria*; where each compound can be representative of a subset of molecules exerting the same binding energy and such as with similar structure to the compound; where the compounds can include higher affinity, as indicated by the binding energy values, than L-carnitine, to the CntA enzymes; etc.).

TABLE 8

Examples of Compounds (e.g., molecules) that can Bind CntA Enzymes of Microorganisms from Proteobacteria and Firmicutes

| Structure | SMILES code | IUPAC nomenclature | Binding Energy (to CntA enzyme, Proteobacteria) | Binding Energy (to CntA enzyme, Firmicutes) |
| --- | --- | --- | --- | --- |
| 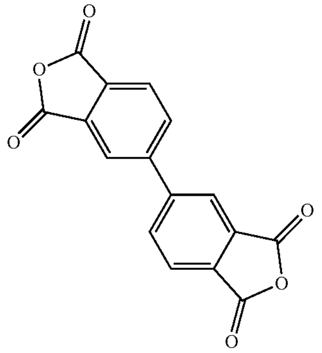 [SMILES: O=C1OC(=O)c2cc(-c3ccc4c(c3)C(=O)OC4=O)ccc21] | c1cc2c(cc1c1ccc3 c(c1)C(=O)OC$_3$ O)C(=O)OC2=O | 4,4'-Biphthalic anhydride | −8.9 kcal/mol | −8.9 kcal/mol |
| 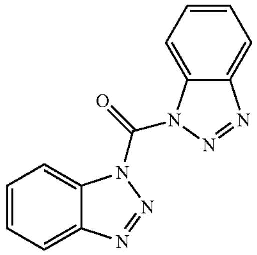 [SMILES: O=C(n1nnc2ccccc21)n1nnc2ccccc21] | O=C(n1nnc2cccc c12)n1nnc2ccccc12 | Bis(1H-benzotriazol-1-yl)methanone | −7.9 kcal/mol | −7.9 kcal/mol |
| 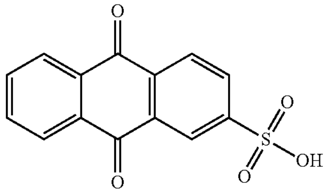 [SMILES: O=C1c2ccccc2C(=O)c2cc(S(=O)(=O)O)ccc21] | c1ccc2c(c1)C(=O) c1ccc(cc1C2=O) S(=O)(=O)O | 2-Anthraquinone-sulfonic acid | −7.8 kcal/mol | −7.8 kcal/mol |
| 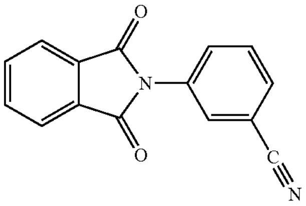 [SMILES: N#Cc1cccc(N2C(=O)c3ccccc3C2=O)c1] | c1ccc2c(c1)C(=O) N(C2=O)c1cccc( c1)C#N | 3-(1,3-Dioxo-1,3-dihydro-2H-(isoindol-2-yl)benzonitrile. | −7.7 kcal/mol | −7.7 kcal/mol |
| 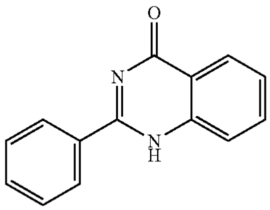 [SMILES: O=c1nc(-c2ccccc2)[nH]c2ccccc12] | c1ccc(cc1)c1nc2c cccc2c(=O)[nH]1 | 2-phenylquinazolin-4-ol | −7.6 kcal/mol | −7.6 kcal/mol |
| 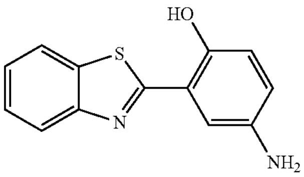 [SMILES: Nc1ccc(O)c(-c2nc3ccccc3s2)c1] | c1ccc2c(c1)nc(s2) c1cc(ccc1O)N | 4-Amino-2-(1,3-benzothiazol-2-yl)phenol | −7.5 kcal/mol | −7.5 kcal/mol |

TABLE 8-continued

Examples of Compounds (e.g., molecules) that can Bind CntA Enzymes of Microorganisms from Proteobacteria and Firmicutes

| Structure | SMILES code | IUPAC nomenclature | Binding Energy (to CntA enzyme, Proteobacteria) | Binding Energy (to CntA enzyme, Firmicutes) |
| --- | --- | --- | --- | --- |
| 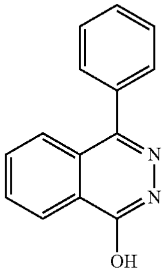 [SMILES: Oc1nnc(-c2ccccc2)c2ccccc12] | c1ccc(cc1)c1c2ccccc2c(=O)[nH]n1 | 4-Phenyl-1(2H)-phthalazinone | −7.4 kcal/mol | −7.4 kcal/mol |
| 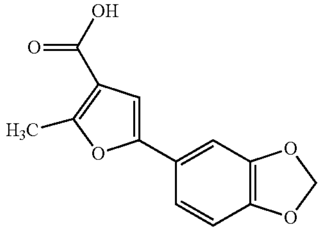 [SMILES: Cc1oc(-c2ccc3c(c2)OCO3)cc1C(=O)O] | Cc1c(cc(o1)c1ccc2c(c1)OCO2)C(=O)O | 5-(1,3-Benzodioxol-5-yl)-2-methyl-3-furoic acid | −7.3 kcal/mol | −7.3 kcal/mol |
| 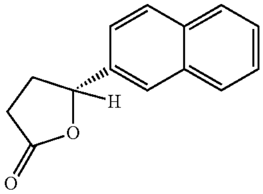 [SMILES: O=C1CC[C@H](c2ccc3ccccc3c2)O1] | c1ccc2cc(ccc2c1)[C@H]1CCC(=O)O1 | (5R)-5-(2-Naphthyl)dihydro-2(3H)-furanone | −7.2 kcal/mol | −7.2 kcal/mol |
| 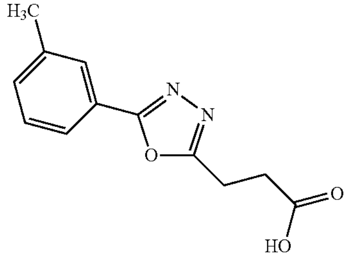 [SMILES: Cc1cccc(-c2nnc(CCC(=O)O)o2)c1] | Cc1cccc(c1)c1nnc(o1)CCC(=O)O | 3-[5-[3-Methylphenyl)-1,3,4-oxadiazol-2-yl]propanoic acid | −7.1 kcal/mol | −7.1 kcal/mol |
| 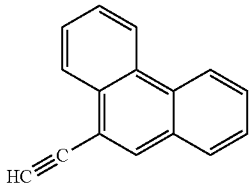 [SMILES: C#Cc1cc2ccccc2c2ccccc12] | C#Cc1cc2ccccc2c2c1cccc2 | 9-ETHYNYL-PHENANTHRENE | −6.9 kcal/mol | −6.9 kcal/mol |
| 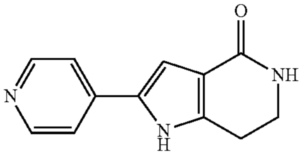 [SMILES: O=C1NCCc2[nH]c(-c3ccncc3)cc21] | c1cnccc1c1cc2c([nH]1)CCNC2=O | PHA-767491 | −6.8 kcal/mol | −6.8 kcal/mol |

TABLE 8-continued

Examples of Compounds (e.g., molecules) that can Bind CntA Enzymes of Microorganisms from Proteobacteria and Firmicutes

| Structure | SMILES code | IUPAC nomenclature | Binding Energy (to CntA enzyme, Proteobacteria) | Binding Energy (to CntA enzyme, Firmicutes) |
| --- | --- | --- | --- | --- |
| 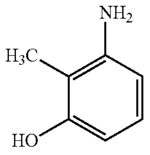 | Cc1c(cccc1O)N | 3-Amino-2-methylphenol | −6.7 kcal/mol | −6.7 kcal/mol |
| 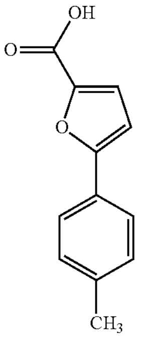 | Cc1ccc(cc1)c1ccc(o1)C(=O)O | 5-(4-Methylphenyl)-2-furoic acid | −6.6 kcal/mol | −6.6 kcal/mol |
| 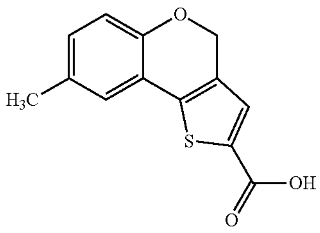 [SMILES: Cc1ccc2c(c1)-c1sc(C(=O)O)cc1CO2] | Cc1ccc2c(c1)c1c(cc(s1)C(=O)O)CO2 | 8-Methyl-4H-thieno[3,2-c] chromene-2-carboxylic acid | −6.5 kcal/mol | −6.5 kcal/mol |
| 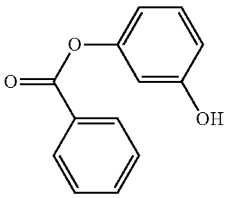 [SMILES: O=C(Oc1cccc(O)c1)c1ccccc1] | c1ccc(cc1)C(=O)Oc1cccc(c1)O | resorcinol monobenzoate | −6.4 kcal/mol | −6.4 kcal/mol |
| 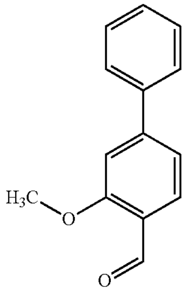 [SMILES: COc1cc(-c2ccccc2)ccc1C=O] | COc1cc(ccc1C=O)c1ccccc1 | 3-Methoxy-4-biphenyl-carbaldehyde | −6.3 kcal/mol | −6.3 kcal/mol |
| 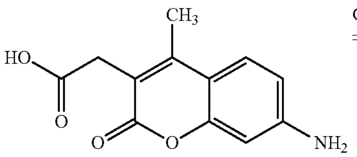 | Cc1c2ccc(cc2oc(=O)c1CC(=O)O)N | (7-Amino-4-methyl-2-oxo-2H-chromen-3-yl)acetic acid | −6.2 kcal/mol | −6.2 kcal/mol |

TABLE 8-continued

Examples of Compounds (e.g., molecules) that can Bind CntA Enzymes of Microorganisms from Proteobacteria and Firmicutes

| Structure | SMILES code | IUPAC nomenclature | Binding Energy (to CntA enzyme, Proteobacteria) | Binding Energy (to CntA enzyme, Firmicutes) |
|---|---|---|---|---|
| 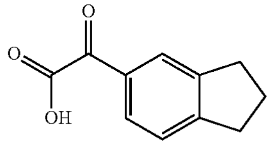 [SMILES: O=C(O)C(=O)c1ccc2c(c1)CCC2] | c1cc2c(cc1C(=O)C(=O)O)CCC2 | 2,3-Dihydro-1H-inden-5-yl(oxo)acetic acid | −6.1 kcal/mol | −6.1 kcal/mol |
| 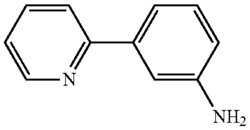 [SMILES: Nc1cccc(-c2ccccn2)c1] | c1ccnc(c1)c1cccc(c1)N | 3-(2-Pyridyl)aniline | −6.0 kcal/mol | −6.0 kcal/mol |
| 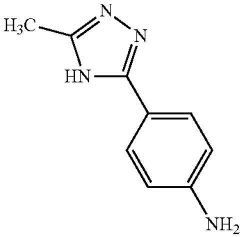 | Cc1nc([nH]n1)c1ccc(cc1)N | 4-(3-Methyl-1H-1,2,4-triazol-5-yl)aniline | −5.9 kcal/mol | −5.9 kcal/mol |
| 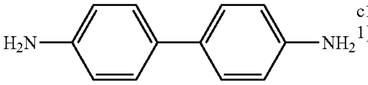 | c1cc(ccc1c1ccc(cc1)N)N | Benzidine | −5.8 kcal/mol | −5.8 kcal/mol |
| 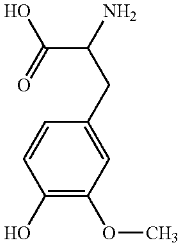 | COc1cc(ccc1O)C[C@@H](C(=O)O)[$NH_3$+] | (DL)-3-0-Methyldopa | −5.7 kcal/mol | −5.7 kcal/mol |
| 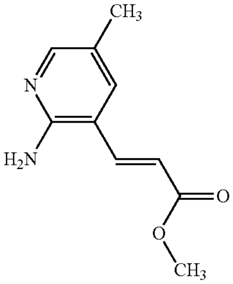 | Cc1cc(c(nc1)N)/C=C/C(=O)OC | Methyl (2E)-3-(2-amino-5-methyl-3-pyridinyl)acrylate | −5.6 kcal/mol | −5.6 kcal/mol |
| 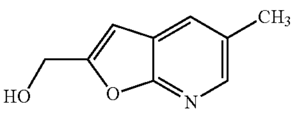 | Cc1cc2cc(oc2nc1)CO | (5-Methylfuro[2,3-b]pyridin-2-yl)methanol | −5.5 kcal/mol | −5.5 kcal/mol |
| 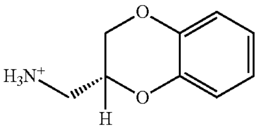 [SMILES: [NH3+]C[C@@H]1COc2ccccc2O1] | c1ccc2c(c1)OC[C@H](O2)C[$NH_3$+] | (2R)-2,3-Dihydro-1,4-benzodion-2-ylmethanaminium | −5.4 kcal/mol | −5.4 kcal/mol |

TABLE 8-continued

Examples of Compounds (e.g., molecules) that can Bind CntA Enzymes of Microorganisms from Proteobacteria and Firmicutes

| Structure | SMILES code | IUPAC nomenclature | Binding Energy (to CntA enzyme, Proteobacteria) | Binding Energy (to CntA enzyme, Firmicutes) |
|---|---|---|---|---|
| 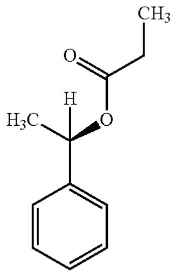 | CCC(=O)O[C@H](C)c1ccccc1 | R-phenylethyl propionate | −5.3 kcal/mol | −5.3 kcal/mol |
| 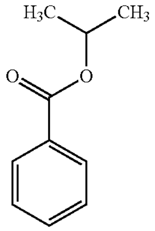 | CC(C)OC(=O)c1ccccc1 | i-propyl benzoate | −5.2 kcal/mol | −5.2 kcal/mol |
| 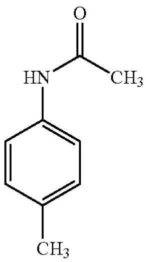 | Cc1ccc(cc1)NC(=O)C | 4-Acetotoluide | −5.1 kcal/mol | −5.1 kcal/mol |
| 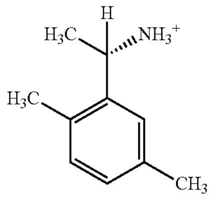 | Cc1ccc(c(c1)[C@H](C)[$NH_3$+])C | Dimethylphenyl) (1S)-1-(2,5-ethanaminium | −5.0 kcal/mol | −5.0 kcal/mol |
| 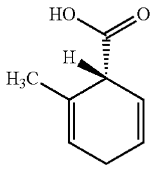 | CC1=CCC=C[C@H]1C(=O)O | (1R)-2-Methyl-2,5-cyclohexadiene-1-carboxylic acid | −4.9 kcal/mol | −4.9 kcal/mol |
| 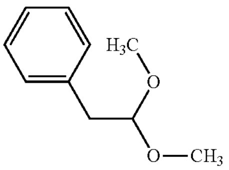 | COC(Cc1ccccc1)OC | (2,2-Dimethoxyethyl) benzene | −4.8 kcal/mol | −4.8 kcal/mol |

In an example, administering to the patient with the one or more conditions can include administering, to the patient with the one or more conditions, a therapeutically effective amount of a compound for inhibiting the CntA enzymes of the microorganisms from *Firmicutes* (phylum) and *Proteobacteria* (phylum), where the compound includes at least one (e.g., any one or more; etc.) of: 4,4'-Biphthalic anhydride; Bis(1H-benzotriazol-1-yl)methanone; 2-Anthraquinonesulfonic acid; 3-(1,3-Dioxo-1,3-dihydro-2H-isoindol-2-yl)benzonitrile; 2-phenylquinazolin-4-ol; 4-Amino-2-(1,3-benzothiazol-2-yl)phenol; 4-Phenyl-1(2H)-phthalazinone; Benzodioxol-5-yl)-2-methyl-3-furoic acid; (5R)-5-(2-Naphthyl)dihydro-2(3H)-furanone; 3-[5-(3-Methylphenyl)-1,3,4-oxadiazol-2-yl]propanoic acid; 9-ETHYNYLPHENANTHRENE; PHA-767491; 3-Amino-2-methylphenol; 5-(4-Methylphenyl)-2-furoic acid; 8-Methyl-4H-thieno[3,2-c]chromene-2-carboxylic acid; resorcinol monobenzoate; 3-Methoxy-4-biphenylcarbaldehyde; (7-Amino-4-methyl-2-oxo-2H-chromen-3-yl)acetic acid; 2,3-Dihydro-1H-inden-5-yl(oxo)acetic acid; 3-(2-Pyridyl) aniline; 4-(3-Methyl-1H-1,2,4-triazol-5-yl)aniline; Benzidine; (DL)-3-O-Methyldopa; Methyl (2E)-3-(2-amino-5-methyl-3-pyridinyl)acrylate; (5-Methylfuro[2,3-b]pyridin-2-yl)methanol; (2R)-2,3-Dihydro-1,4-benzodioxin-2-ylmethanaminium; R-phenylethyl propionate; i-propyl benzoate; 4-Acetotoluide; (1S)-1-(2,5-Dimethylphenyl) ethanaminium; (1R)-2-Methyl-2,5-cyclohexadiene-1-carboxylic acid; (2,2-Dimethoxyethyl)benzene; and pharmaceutically acceptable forms thereof (e.g., derivatives thereof; pharmaceutically deliverable forms thereof; etc.); and/or salts (e.g., pharmaceutically acceptable salts; etc.) thereof. In an example, compounds including different binding affinities (and/or other suitable interaction parameters) to CntA enzymes depending on the association of the CntA enzyme to a given taxon (e.g., CntA enzymes of microorganisms from *Proteobacteria*; CntA enzymes of microorganisms from *Firmicutes*; etc.), and/or compounds with different affinities generally, can enable different applications, such as where a compound with high affinity can exert an irreversible inhibition on the CntA enzyme. However, compounds for inhibiting CntA enzymes of microorganisms from *Firmicutes* (phylum) and *Proteobacteria* (phylum) can be configured in any suitable manner, and administering such compounds can be performed in any suitable manner (e.g., for affecting any suitable targets).

However, compounds can be configured in any suitable manner, and administering one or more compounds S110 can be performed in any suitable manner.

2.2 Determining a Representative Sequence.

Additionally or alternatively, embodiments of the method 100 can include determining one or more representative sequences of one or more targets (e.g., CutC enzymes; CntA enzymes; other enzymes; proteins; other biological targets; non-biological targets; enzymes associated with at least one of TMA, TMAO, and/or derivatives thereof; etc.) S120, which can function to determine representative characteristics of targets for use in modeling and/or experiments for facilitating compound determination.

Representative sequences and/or characteristics can include any one or more of nucleic acid sequence and/or composition; amino acid sequence and/or composition; functional characteristics; structural characteristics (e.g., multidimensional structure; etc.); evolutionary characteristics; and/or other suitable characteristics.

Representative sequences and/or characteristics are preferably determined for one or more targets, but can additionally or alternatively be determined for one or more of control molecules, compounds, and/or any other suitable molecules. In an example representative sequences and/or characteristics can be determined for one or more enzymes, such as where the enzyme can include at least one CutC enzyme and CntA enzyme, and where the representative sequence can be representative of a set of sequences of the enzyme for at least one taxon including at least one of *Firmicutes* (phylum) and *Proteobacteria* (phylum).

Representative sequences and/or characteristics are preferably representative for one or more taxons from a set of microorganism taxa. For example, a representative sequence can be representative of a set of sequences of one or more targets (e.g., CutC enzyme, CntA enzyme, etc.) for one or more microorganism taxa (e.g., *Firmicutes* and/or *Proteobacteria* and/or other suitable taxa; etc.). In an example, determining one or more representative sequences can include: generating a sequence similarity network with target sequences (e.g., CutC enzyme sequences; CntA enzyme sequences; etc.) associated with (e.g., belonging to; of microorganisms belonging to; etc.) each taxon of the set of taxa (e.g., associated with both *Firmicutes* and *Proteobacteria*), such as in order to identify a representative target sequence for each taxon (e.g., a first representative CutC enzyme sequence for *Firmicutes* and a second representative CutC enzyme sequence for *Proteobacteria*; a first representative CntA enzyme sequence for *Firmicutes* and a second representative CntA enzyme sequence for *Proteobacteria*; etc.).

However, determining one or more representative sequences S120 can be performed in any suitable manner.

2.3 Generating a Model.

Additionally or alternatively, embodiments of the method 100 can include generating one or more models (e.g., protein structure models; etc.) of the one or more targets based on the one or more representative sequences of the one or more targets S130, which can function to model one or more targets for facilitating experiments useful in compound determinations.

Models preferably include protein structure models (e.g., modeling enzyme targets such as CntA enzymes and/or CutC enzymes; etc.), but can additionally or alternatively include any suitable models (e.g., modeling any suitable types of targets; etc.). Models can include any one or more of computational models, models of any suitable number of dimensions, non-computational models, physical models, virtual reality models, augmented reality models, and/or any suitable types of models. Models can be generating using any suitable processing operations and/or artificial intelligence approaches described herein.

Generating models is preferably based on representative sequences, such as where characteristics of the representative sequences can be used as inputs and/or parameters for model generation. For example, generating models can include generating protein structure models for both the CutC enzyme from *Firmicutes* (e.g., Uniprot ID: CoD5P1) (e.g., based on the representative sequence for the CutC enzyme from microorganisms from *Firmicutes*; etc.) and CutC enzyme from *Proteobacteria* (e.g., Uniprot ID: B4EYG1) (e.g., based on the representative sequence for the CutC enzyme from microorganisms from *Proteobacteria*; etc.) using a homology modeling approach (and/or any suitable modeling approach), which can facilitate determination of 3D models (e.g., for proteins lacking crystallographic data; etc.). For example, generating models can include generating protein structure models for both the CntA enzyme from *Firmicutes* (e.g., Uniprot ID: J3B3E2) (e.g., based on the representative sequence for the CntA enzyme from microorganisms from *Firmicutes*; etc.) and CntA enzyme from *Proteobacteria* (e.g., Uniprot ID: L1LUC3) (e.g., based on the representative sequence for the CntA enzyme from microorganisms from *Proteobacteria*; etc.) using a homology modeling approach (and/or any suitable modeling approach), which can facilitate determination of 3D models (e.g., for proteins lacking crystallographic data; etc.).

However, generating one or more models S130 can be performed in any suitable manner.

2.4 Determining an Interaction Parameter Associated with a Control.

Additionally or alternatively, embodiments of the method 100 can include determining one or more control binding parameters (and/or other suitable interaction parameters; etc.) to the one or more targets based on one or more experiments with the one or more models and one or more control molecules S140, which can function to determine characteristics describing interactions between one or more controls and one or more targets.

Types of binding parameters (e.g., control binding parameters; compound binding parameters; etc.) preferably include types of binding parameters included in Tables 1-8 (e.g., binding energy values, affinity energy values, etc.), but can additionally or alternatively include association rate, dissociation rate, half-life of interaction (e.g., between receptor and peptide), binding constants, binding specificity, thermodynamics associated parameters (e.g. enthalpy, entropy, Gibbs free energy), parameters associated with number and type of binding sites (e.g., stoichiometry), parameters associated with undesired binding (e.g., self-assembly, interference with other proteins, etc.), and/or any other suitable binding parameters. include any suitable binding affinity parameters. Interaction parameters preferably include binding affinities, but can additionally or alternatively include any suitable parameters associated with control molecules, compounds, targets, and/or other suitable molecules, and/or associated with interactions between any combination of such molecules.

Experiments preferably include docking simulations (e.g., docking simulations using the one or more models and simulating the binding of one or more control molecules to the one or more models, such as to the active sites of one or more of the protein structure models for CutC enzymes and/or CntA enzymes; etc.), but can additionally or alternatively include one or more of: other computational simulations (e.g., in silico, etc.); in vitro experiments, in vivo experiments, benchtop experiments, use of computational models, and/or any other suitable other experiments.

In an example, docking simulations can be performed to determine control binding parameters (e.g., binding energy values for the control molecules; etc.) for choline and DMB in relation to binding CutC enzymes of microorganisms from different taxa (e.g., *Firmicutes* and/or *Proteobacteria*; etc.), such as based on performing docking simulations with generated models of the CutC enzymes for the different taxa (e.g., a first model of the CutC enzyme from *Firmicutes*; a second model of the CutC enzyme from *Proteobacteria*; etc.) and simulating control molecule (e.g., choline and/or DMB) binding to the generated models. In specific examples, docking simulations can result in binding energy values of −3.7 kcal/mol for choline in relation to CutC enzyme from *Firmicutes;* −4.8 kcal/mol for DMB in relation to CutC enzyme from *Firmicutes;* −4.1 kcal/mol for choline in relation to CutC enzyme from *Proteobacteria*; and −5.2 kcal/mol for DMB in relation to CutC enzyme from *Proteobacteria*, such as where such binding energy values can indicate a greater affinity of binding for DMB than for choline (e.g., in the context of competitive inhibition; etc.)

In an example, docking simulations can be performed to determine control binding parameters (e.g., binding energy values for the control molecules; etc.) for L-carnitine in relation to binding CntA enzymes of microorganisms from different taxa (e.g., *Firmicutes* and/or *Proteobacteria*; etc.), such as based on performing docking simulations with generated models of the CntA enzymes for the different taxa (e.g., a first model of the CntA enzyme from *Firmicutes*; a second model of the CntA enzyme from *Proteobacteria*; etc.) and simulating control molecule (e.g., L-carnitine; DMB; etc.) binding to the generated models. In specific examples, docking simulations can result in binding energy values of −4.5 kcal/mol for L-carnitine in relation to CntA enzyme from *Firmicutes;* −4.8 kcal/mol for DMB in relation to CntA enzyme from *Firmicutes;* −4.3 kcal/mol for L-carnitine in relation to CntA enzyme from *Proteobacteria*; and −5.2 kcal/mol for DMB in relation to CntA enzyme from *Proteobacteria.*

Additionally or alternatively, docking simulations can be performed with any suitable models in relation to any suitable control molecules and/or any suitable molecules.

In examples, determining interaction parameters associated with controls and/or associated with compounds (e.g., in relation to S150), and/or any suitable portions of embodiments of the method 100 (e.g., determining representative sequences Silo; generating models S120; etc.) can apply one or more of: extracting features, performing pattern recognition on data, fusing data from multiple sources, combination of values (e.g., averaging values, etc.), compression, conversion (e.g., digital-to-analog conversion, analog-to-digital conversion), performing statistical estimation on data (e.g. ordinary least squares regression, non-negative least squares regression, principal components analysis, ridge regression, etc.), wave modulation, normalization, updating, ranking, weighting, validating, filtering (e.g., for baseline correction, data cropping, etc.), noise reduction, smoothing, filling (e.g., gap filling), aligning, model fitting, binning, windowing, clipping, transformations, mathematical operations (e.g., derivatives, moving averages, summing, subtracting, multiplying, dividing, etc.), data association, multiplexing, demultiplexing, interpolating, extrapolating, clustering, image processing, signal processing, visualizing, and/or any other suitable processing operations.

In examples, determining interaction parameters associated with controls and/or associated with compounds (e.g., in relation to S150), and/or any suitable portions of embodiments of the method 100 (e.g., determining representative sequences Silo; generating models S120; etc.) can apply artificial intelligence approaches (e.g., machine learning approaches, etc.) including any one or more of: supervised learning (e.g., using logistic regression, using back propagation neural networks, using random forests, decision trees, etc.), unsupervised learning (e.g., using an Apriori algorithm, using K-means clustering), semi-supervised learning, a deep learning algorithm (e.g., neural networks, a restricted Boltzmann machine, a deep belief network method, a convolutional neural network method, a recurrent neural network method, stacked auto-encoder method, etc.), reinforcement learning (e.g., using a Q-learning algorithm, using temporal difference learning), a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4-5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a dimensionality reduction method (e.g., principal component analysis, partial lest squares regression, Sammon mapping, multidimensional scaling, projection pursuit, etc.), an ensemble method (e.g., boosting, bootstrapped aggregation, AdaBoost, stacked generalization, gradient boosting machine method, random forest method, etc.), and/or any suitable artificial intelligence approach.

Control molecules preferably include one or more of choline, DMB, and/or L-carnitine, but can additionally or alternatively include any suitable substrates that bind to any suitable targets (e.g., substrates binding to CutC enzymes and/or CntA enzymes; etc.), any suitable molecules associated with any suitable targets and/or conditions, and/or any suitable molecules.

However, determining interaction parameters associated with one or more controls S140 can be performed in any suitable manner.

2.5 Determining an Interaction Parameter Associated with a Compound.

Additionally or alternatively, embodiments of the method 100 can include determining a set of compound binding parameters (and/or other suitable interaction parameters; etc.) to the one or more targets based on a set of experiments with the one or more models and a library of compounds (e.g., with the potential to affect the one or more targets, such as the potential to inhibit CutC enzymes and/or CntA enzymes; etc.) S150, which can function to determine characteristics describing interactions between one or more compounds (e.g., potential compounds, etc.) and one or more targets.

Compound binding parameters are preferably determined for a library of compounds including any suitable number of compounds. Determining the library of compounds can be based on any suitable parameters (e.g., similarity to structures, number of atoms, and/or other suitable characteristics of control molecules, molecules naturally associated with one or more targets, and/or other suitable molecules; databases of molecules; number of compounds; type of targets; type of conditions; molecules that do not infringe Lipinski rules of druggability; etc.). In an example, determining a library of compounds can include selecting only compounds with a number of atoms similar to (e.g., within a threshold of) a number of atoms of choline, DMB, and/or L-carnitine (e.g., within a limit of 28 atoms; etc.). In a specific example, the library of compounds can include around 24,000 molecules, but can include any suitable number of molecules.

Determining compound binding parameters and/or other interaction parameters is preferably based on a set of experiments (e.g., types of experiments described in relation to S140), such as based on docking simulations using the one or more generated models (e.g., models for CutC and CntA enzymes for *Firmicutes* and *Proteobacteria*) and simulating binding by the compounds in relation to the models.

Determining compound binding parameters can be used to determine the binding parameters included in Tables 1-8.

Determining compound binding parameters can be performed in a same, similar, analogous, or different manner than determining control binding parameters.

However, determining interaction parameters associated with one or more compounds S150 can be performed in any suitable manner.

2.6 Identifying a Compound.

Additionally or alternatively, embodiments of the method 100 can include identifying at least one compound (e.g., from the library of compounds; etc.), based on the one or more control binding parameters and the set of compound binding parameters S160, which can function to identify at least one compound for treating a patient with a condition associated with at least one of trimethylamine (TMA), trimethylamine N-oxide (TMAO), and derivatives thereof, and/or for treating a patient with any suitable conditions.

Identifying compounds is preferably based on a comparison between one or more control binding parameters and the set of compound binding parameters (e.g., filtering a library of compounds for compounds with corresponding compound binding parameters greater than one or more of the control binding parameters, etc.). Additionally or alternatively, identifying compounds can be based on control binding parameters and compound binding parameters in any suitable manner, and/or can be based on an y suitable interaction parameters associated with the one or more control molecules and/or any suitable interaction parameters associated with the compounds.

In an example, identifying compounds can include selecting, from a library of compounds (e.g., selected based on atom number similarity to choline and/or DMB, within a limit of 28 atoms; etc.), compounds with equal or greater binding affinity (e.g., as indicated by binding energy value; etc.) for CutC enzymes than choline. In an example, compounds (e.g., with equal or greater binding affinity for CutC enzymes than choline; etc.) can be filtered (e.g., further filtered; etc.) based on non-infringement (e.g., non-violation; etc.) of Lipinski rules of druggability, such as including molecular weight$<$500 Daltons, number of H-bonds donor$<$5, number of H-bonds acceptor$<$10, number of N and O atoms$<$15, range of partition coefficient log P between −2 and 5, number of rotatable bonds$<$10, number of ring number$<$10. In an example, compounds (e.g., equal or greater binding affinity for CutC enzymes than choline, and/or not violating Lipinski rules of druggability; etc.) can be filtered (e.g., further filtered; etc.) out if the molecule includes any atoms different from C—H—O—N atoms.

In an example, identifying compounds can include selecting, from a library of compounds (e.g., selected based on atom number similarity to choline, DMB, and/or L-carnitine, within a limit of 28 atoms; etc.), compounds with equal or greater binding affinity (e.g., as indicated by binding energy value; etc.) for CntA enzymes than L-carnitine. In an example, compounds (e.g., with equal or greater binding affinity for CntA enzymes than L-carnitine; etc.) can be filtered (e.g., further filtered; etc.) based on non-infringement (e.g., non-violation; etc.) of Lipinski rules of druggability, such as including molecular weight$<$500 Daltons, number of H-bonds donor$<$5, number of H-bonds acceptor$<$10, number of N and O atoms$<$15, range of partition coefficient log P between −2 and 5, number of rotatable bonds$<$10, number of ring number$<$10. In an example, compounds (e.g., equal or greater binding affinity for CntA enzymes than L-carnitine, and/or not violating Lipinski rules of druggability; etc.) can be filtered (e.g., further filtered; etc.) out if the molecule includes any atoms different from C—H—O—N atoms.

In examples, applying such criteria (and/or any suitable criteria) in determining compounds can result in any suitable compounds included in Tables 1-8, such as DMB analogues (e.g., with Tanimoto coefficient>=0.8, and with equal or greater binding affinity than DMB to CutC enzymes from *Firmicutes* and *Proteobacteria*; as shown in Table 1; etc.), such as L-carnitine analogues (e.g., with Tanimoto coefficient>=0.7, and with equal or greater binding affinity than L-carnitine to CntA enzymes from *Firmicutes* and *Proteobacteria*; as shown in Table 5; etc.).

Identified compounds are preferably usable for treating patients with one or more conditions associated with the at least one of TMA, TMAO, and derivatives thereof, and/or for treating patients with any suitable conditions. For example, identified compounds can be used in administering a therapeutically effective amount of the one or more compounds (e.g., in relation to S110). Additionally or alternatively, identified compounds can be used for any suitable purpose.

However, identifying compounds S160 can be performed in any suitable manner.

2.7 Validating a Compound.

Additionally or alternatively, embodiments of the method 100 can include validating one or more compounds S170, which can function to experimentally validate and/or otherwise test one or more compounds.

Any suitable compounds described herein can be validated (e.g., experimentally tested, etc.). Compounds can preferably be validated in relation to effect on one or more targets (e.g., CutC enzymes, CntA enzymes, etc.). For example, compounds can be validated in relation to ability of the compounds to inhibit conversion of choline (e.g., in the context of CutC enzymes, etc.) or L-carnitine (e.g., in the context of CntA enzymes) into trimethylamine (TMA) by gut microbiota. As such, compounds can be validated in relation to their ability to treat one or more conditions associated with at least one of trimethylamine (TMA), trimethylamine N-oxide (TMAO), and/or derivatives thereof. However, any suitable molecules described herein can be validated for any suitable purpose, such as by applying any one or more techniques described herein.

In examples, experiments are carried out using cultures of bacterial strains that produce either CutC/CutD or CntA/CntB enzymes. As an example, cultures of *Acinetobacter baumanii* (*Proteobacteria*, aerobic, CntA/CntB producer), *Proteus mirabilis*, (*Proteobacteria*, anaerobic, CutC/CutD producer), *Sporosarcina newyorkensis* DSM 23540 (*Firmicutes*, CntA/CntB producer, aerobic) and/or *Streptococcus dysgalactiae* DSM23147 (*Firmicutes*, CutC/CutD producer, anaerobic) can be used.

In an example, an experimental setup includes evaluation of the gradual consumption of either choline and/or L-carnitine, and/or the progressive production of TMA. In a specific example, to quantify the production of (TMA), cultures are set up in triplicate in cell culture flasks, using medium supplemented with carnitine or choline (depending on the case) as a sole carbon source; a sample is taken from each flask at different time points (e.g., t=0, 4, 8, 12, 24 and 48 h; any suitable time points); optical density at 600 nm is obtained for each sample; and TMA, carnitine, and/or choline are quantified for each sample (e.g., corresponding to the different time points; etc.). L-carnitine and choline can quantified in each sample using standard quantification kits (e.g., MAK056 and MAK063, Sigma-Aldrich). TMA quantification can be carried out using cation exchange ion chromatography equipped with a separation column and a conductivity detector.

Additionally or alternatively, CutC or CntA TMA lyase activity can be quantified in vitro by incubating, for example: a cell lysate (typically ~3 mg protein), an isolated enzyme (typically ~30 μg protein), cultured live microbe ($OD_{600\ nm}$~1.0), and/or over cecal lysate with a d9-labeled synthetic substrate (100 μM, choline or L-carnitine, during 10-16 h). In such cases, TMA lyase activity can be monitored by quantifying d9-TMA production by LC/MS/NIS analysis. Additionally or alternatively, TMA production can be detected from supernatants of the culture cells, using cation-exchange ion chromatography. However, any suitable quantification techniques can be applied, such as for validating one or more compounds.

In a specific example, with obtained baselines of the consumption of L-carnitine and/or choline, and/or the production of TMA, a dose response curve of the control compound DMB (e.g., after incubation by 10-16 h) can be obtained on each culture to verify decrease of TMA production; and one or more dose response curves can be obtained for each compound (e.g., described in Tables 1-8; described herein; etc.), such as by incubating the compounds (e.g., 10-16 h) into the corresponding intact cell cultures (e.g., where cell lysates and/or isolated enzymes can additionally or alternatively be used), using as substrates L-carnitine and/or choline at different concentrations (e.g., as an example, 20, 40, 60, 80, 100 μM), and then measuring the TMA production at each point. In specific examples, a typical concentration used for the compounds to inhibit production of TMA in an intact cell culture is at the scale of ~1 mM. In specific examples, compounds reduced TMA production by −50% or more at each tested point.

In a specific example, experiments applying techniques described above can be performed in *Escherichia coli* lysates expressing either CutC/CutD or CntA/CntB enzymes from *Proteobacteria* and/or *Firmicutes* bacteria species mentioned above.

In a specific example, TMA lyase (CutC/CntA) inhibitory ability, or IC50, under the presence of claimed compounds can be assessed over isolated enzymes lysates (e.g., at the scale of ~30 ug), where enzymes can be expressed in a model organism (e.g., *E. coli* Top10) and later purified. In a specific example, one or more dose response curves can be generated by testing compounds over the isolated enzymes lysates in increasing concentrations in the range between 1 and 1000 μM. In specific examples, IC50 values of compounds are in the range of ~10 μM.

3. Other.

Any of the variants described herein (e.g., embodiments, variations, examples, specific examples, figures, etc.) and/or any portion of the variants described herein can be additionally or alternatively combined, aggregated, excluded, used, performed serially, performed in parallel, and/or otherwise applied.

Portions of embodiments of the method 100 and/or system 200 can be embodied and/or implemented at least in part as a machine configured to receive a computer-readable medium storing computer-readable instructions. The instructions can be executed by computer-executable components that can be integrated with the system 200. The computer-readable medium can be stored on any suitable computer-readable media such as RAMs, ROMs, flash memory, EEPROMs, optical devices (CD or DVD), hard drives, floppy drives, or any suitable device. The computer-executable component can be a general or application specific processor, but any suitable dedicated hardware or hardware/firmware combination device can alternatively or additionally execute the instructions.

As a person skilled in the art will recognize from the previous detailed description and from the figures and claims, modifications and changes can be made to embodiments of the method 100, system 200, and/or variants without departing from the scope defined in the claims.

We claim:

1. A computer-implemented method for identifying at least one compound for treating a patient with a condition associated with at least one of trimethylamine (TMA), trimethylamine N-oxide (TMAO), or derivatives thereof, the method comprising:

determining, by one or more processors, a representative sequence of an enzyme associated with the at least one of TMA, TMAO, and derivatives thereof, wherein the representative sequence is representative of a set of sequences of the enzyme for at least one taxon from a set of microorganism taxa;

generating, by the one or more processors, a protein structure model of the enzyme based on the representative sequence of the enzyme;

determining, by the one or more processors, a control binding parameter to the enzyme based on a control docking simulation with the protein structure model and a control molecule;

determining, by the one or more processors, using a machine learning algorithm, a set of compound binding parameters to the enzyme based on a set of compound docking simulations with the protein structure model and a library of compounds; and identifying, by the one or more processors, the at least one compound, from the library of compounds, for treating the patient with the condition associated with the at least one of TMA, TMAO, and derivatives thereof, based on a comparison between the control binding parameter and the set of compound binding parameters.

2. The method of claim 1, wherein the enzyme comprises at least one of choline trimethylamine-lyase (CutC) enzyme or Rieske-type oxygenase (CntA) enzyme, and wherein the at least one taxon comprises at least one of *Firmicutes* or *Proteobacteria.*

3. The method of claim 2, wherein the at least one compound comprises at least one of Methyl 4-methyl-4-piperidinecarboxylate; Methyl heptanoate; 3-Methylpyridazine; 4,5-Dimethyl-1,2-oxazol-3-amine; 2-(2-Hydroxyethoxy)phenol; 2-Hydroxy-N-(3-pyridinylmethyl) ethanaminium; 3-Phenyl-1-propanol; (2R)-6-Methyl-2-heptanol; 2-Phenoxyacetohydrazide; N-Hydroxyoctanamid; Cyclobutanecarbohydrazide; Phenylhydrazine; (1S,4R)-2-Azabicyclo[2.2.1]hept-5-en-3-one; salicylamide; Adamantane; 3-Azabicyclo[3.3.1]nonane; N-Hydroxy-2-methylbenzenecarboximidamide; (−)-camphene; (1S,2S,4S)-Bicyclo [2.2.1]hept-5-en-2-ylmethanol; Dicyclopentadiene; (8-anti)-3-Azabicyclo[3.2.1]octan-8-ol; (1R,2S,6R,7S)-Tricyclo [5.2.1.02,6]deca-3,8-diene; pharmaceutically acceptable forms thereof; or salts thereof.

4. The method of claim 3, wherein the condition comprises at least one of a cardiovascular condition, a renal condition, a metabolic-related condition, or a nutrition-related condition.

5. The method of claim 2, wherein the at least one compound comprises at least one of 2-Ethyl-1-butanol; (2R)-3,3-Dimethyl-1,2-butanediol; (2S)-3,3-Dimethyl-1,2-butanediol; (2S)-4-Methyl-2-pentanol; (2S)-3-Methyl-2-butanol; (2R)-4-Methyl-2-pentanol; (2R)-3-Methyl-2-butanol; (2S)-2-Pentanol; (2S)-2-Methyl-1,4-butanediol; 2-Methyl-2,4-butanediol; Trimethylolpropane; pharmaceutically acceptable forms thereof; or salts thereof.

6. The method of claim 2, wherein the at least one compound comprises at least one of 3-(4-Methoxyphenyl) propanal; 1-(3-Pyridinyl)-2-propanamine; 2-[(2R)-2-Butanyl]phenol; 4-Propylbenzoic acid; (2S)-1-(Benzyloxy)-2-propanol; Methyl 3-(4-hydroxyphenyl)propanoate; α-Methylphenyl alanine; 2,2-Dimethyl-1-phenyl-1-propanol; Methyl (2R)-hydroxy(phenyl)acetate; (2S)-2-Phenylpyrrolidinium; 4-Methyl-3-phenyl-1,2-oxazol-5-amine; 4,4'-Biphenyldiamine; 4'-Methyl-2 biphenylcarbonitrile; 4-Biphenylol; 2-[3-(4-Methylphenyl)-1,2-oxazol-5-yl]thanol; 4-Biphenylcarboxamide; 4-Ethynylbiphenyl; 5-(4-Methylphenyl)-1H-1,2,4-triazol-3-amine; 5-(4-Methylphenyl)-1H-pyrazol-3-amine; 4-Hydroxycatechol; 3-Phenyl-1H-pyrazole-5-carbohydrazide; 4-Methyl-1,3-benzenediol; pharmaceutically acceptable forms thereof; or salts thereof.

7. The method of claim 2, wherein the at least one compound comprises at least one of N-(2-Hydroxyethyl)-1, 3-propanediaminium; 3-Methoxy-3-methylbutanol; 4-Pyridinylmethanaminium; N-Methyl-3-pyridinamine; 2-Methoxypyridine; 5-Methyl-3-pyridinamine; 1-(4-Methyl-3-pyridinyl)methanamine; Mesitylene; (E)-Benzaldoxime' (3R)-2,2,4-Trimethyl-1,3-pentanediol; (1R,4R)-2-Azabicyclo[2.2.1]hept-2-ylacetic acid; 3-ACETYLPHENOL; 3-Hydroxybenzoicacid; 1H-Indol-7-ylmethanol; 3-Vinylaniline; (3s,5s,7s)-1-Isocyanatoadamantane; (1R,2S,5R)-2-Hydroxy-2,6,6-trimethylbicyclo[3.1.1] heptan-3-one; (−)β-Pinene; 2H-Isoindole-1,3-diamine; (3s, 5s,7s)-1-Adamantanol; (3-Aminobicyclo[2.2.1]hept-2-yl) methanol; 3-(Hydrazinomethyl)phenol; (1S,2R)-2-Carbamoylcyclohexanaminium; (1S,4R)-1,3,3-Trimethylbicyclo[2.2.1]heptan-2-one; (1R,4S)-1,3,3-Trimethylbicyclo[2.2.1]heptan-2-one; pharmaceutically acceptable forms thereof; or salts thereof.

8. The method of claim 2, wherein the at least one compound comprises at least one of N-Methylglutamic acid; 4-(1-Pyrrolidinyl)butanoic acid; 4-Methyl-4-piperidinecarboxylic acid; Isonipecotic acid; pharmaceutically acceptable forms thereof; or salts thereof.

9. The method of claim 2, wherein the at least one compound comprises at least one of N-propylbenzene; N-Ethyl-2-pyridinamine; (4R)-4-Amino-1-propyl-2-pyrrolidinone; 2,5-Diaminotoluene; Ethyl phenyl ether; Phenylcyanate; 1-(2-Cyclopenten-1-yl)acetone; 2-Amino-3-methylpyridinium; E-pyridine-3-aldoxime; N-Cyclohexylformamide; 2-Methyl-2-hexenoic acid; 4-Heptanaminium; pharmaceutically acceptable forms thereof; or salts thereof.

10. The method of claim 2, wherein the at least one compound comprises at least one of 3,4-Anhydro-3-carboxy-2-deoxy-L-threo-pentaric acid; 2,2'-[(2-Hydroxyethyl) imino]diacetic acid; 1H-Tetrazol-5-ylacetic acid; Diacetylacetone; (2S)-2-Acetoxypropanoic acid; pharmaceutically acceptable forms thereof; or salts thereof.

11. The method of claim 2, wherein the at least one compound comprises at least one of 4,4'-Biphthalic anhydride; Bis(1H-benzotriazol-1-yl)methanone; 2-Anthraquinonesulfonic acid; 3-(1,3-Dioxo-1,3-dihydro-2H-isoindol-2-yl)benzonitrile; 2-phenylquinazolin-4-ol; 4-Amino-2-(1, 3-benzothiazol-2-yl)phenol; 4-Phenyl-1(2H)-phthalazinone; Benzodioxol-5-yl)-2-methyl-3-furoic acid; (5R)-5-(2-Naphthyl)dihydro-2(3H)-furanone; 3-[5-(3-Methylphenyl)-1,3,4-oxadiazol-2-yl]propanoic acid; 9-ETHYNYLPHENANTHRENE; PHA-767491; 3-Amino-2- methylphenol; 5-(4-Methylphenyl)-2-furoic acid; 8-Methyl-4H-thieno[3,2-c]chromene-2-carboxylic acid; resorcinol monobenzoate; 3-Methoxy-4-biphenylcarbaldehyde; (7-Amino-4-methyl-2-oxo-2H-chromen-3-yl)acetic acid; 2,3-Dihydro-1H-inden-5-yl(oxo)acetic acid; 3-(2-Pyridyl) aniline; 4-(3-Methyl-1H-1,2,4-triazol-5-yl)aniline; Benzidine; (DL)-3-O-Methyldopa; Methyl (2E)-3-(2-amino-5-methyl-3-pyridinyl)acrylate; (5-Methylfuro[2,3-b]pyridin-2-yl)methanol; (2R)-2,3-Dihydro-1,4-benzodioxin-2-ylmethanaminium; R-phenylethyl propionate; i-propyl benzoate; 4-Acetotoluide; (1S)-1-(2,5-Dimethylphenyl) ethanaminium; (1R)-2-Methyl-2,5-cyclohexadiene-1-carboxylic acid; (2,2-Dimethoxyethyl)benzene; pharmaceutically acceptable forms thereof; or salts thereof.

* * * * *